United States Patent
Kim et al.

(10) Patent No.: US 9,884,308 B2
(45) Date of Patent: Feb. 6, 2018

(54) METAL-ORGANIC FRAMEWORKS AND PROCESS OF PREPARING THE SAME

(71) Applicant: KOREA INSTITUTE OF ENERGY RESEARCH, Daejeon (KR)

(72) Inventors: Hyunuk Kim, Daejeon (KR); Hee-yeon Kim, Daejeon (KR); Young Cheol Park, Daejeon (KR); Jong-ho Moon, Seoul (KR); Dong-hyuk Chun, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 0 days.

(21) Appl. No.: 15/095,701

(22) Filed: Apr. 11, 2016

(65) Prior Publication Data

US 2017/0106348 A1 Apr. 20, 2017

(30) Foreign Application Priority Data

Oct. 14, 2015 (KR) ........................ 10-2015-0143596

(51) Int. Cl.
| | | |
|---|---|---|
| *B01J 20/22* | (2006.01) | |
| *B01J 20/28* | (2006.01) | |
| *C07F 15/06* | (2006.01) | |
| *C07F 15/04* | (2006.01) | |
| *C07F 15/02* | (2006.01) | |
| *C07F 13/00* | (2006.01) | |
| *C07F 1/00* | (2006.01) | |
| *C07F 3/00* | (2006.01) | |

(52) U.S. Cl.
CPC ....... *B01J 20/226* (2013.01); *B01J 20/28066* (2013.01); *B01J 20/28073* (2013.01); *C07F 1/005* (2013.01); *C07F 3/003* (2013.01); *C07F 13/005* (2013.01); *C07F 15/025* (2013.01); *C07F 15/045* (2013.01); *C07F 15/065* (2013.01); *B01D 2253/204* (2013.01); *B01D 2257/502* (2013.01); *B01D 2257/504* (2013.01)

(58) Field of Classification Search
None
See application file for complete search history.

(56) References Cited

U.S. PATENT DOCUMENTS

2007/0248852 A1* 10/2007 Mueller ................ B01J 20/226
95/90

OTHER PUBLICATIONS

Britt, D. et al. PNAS, 2009, vol. 106, No. 49, supporting index, 10 pages.*
Queen, W.L., et al., "Comprehensive study of carbon dioxide adsorption in the metal-organic frameworks M2(dobdc) (M ¼ Mg, Mn, Fe, Co, Ni, Cu, Zn)," Chem. Sci., 2014, vol. 5, pp. 4569-4581.

(Continued)

*Primary Examiner* — Clinton Brooks
(74) *Attorney, Agent, or Firm* — Duane Morris LLP; J. Rodman Steele, Jr.; Gregory M. Lefkowitz

(57) ABSTRACT

The present disclosure relates to a metal-organic framework and a method for preparing the same. In accordance with the present disclosure, a metal-organic framework having large specific surface area can be prepared and the prepared porous material exhibits high carbon dioxide and carbon monoxide adsorption characteristics at room temperature.

3 Claims, 16 Drawing Sheets

(56) References Cited

OTHER PUBLICATIONS

Caskey, S.R., et al., "Dramatic Tuning of Carbon Dioxide Uptake via Metal Substitution in a Coordination Polymer with Cylindrical Pores," J. Am. Chem. Soc., 2008, vol. 130, pp. 10870-10871.

Dietzel, P.D.C., et al., "Base-Induced Fonnation of Two-Magnesium Metal-Organic Framework Compounds with a Bifunctional Tetratopic Ligand," Eur. J. Inorg. Chem., 2008, pp. 3624-3632.

Britt, D., et al., "Highly efficient separation of carbon dioxide by a metal-organic framework replete with open metal sites," PNAS, 2009, vol. 106, No. 49, pp. 20637-20640.

Dietzel et al., "Application of metal-organic frameworks with coordinatively unsaturated metal sites in storage and separation of methane and carbon dioxide", J. Mater. Chem., 19, Aug. 21, 2009, pp. 7362-7370.

Disseration, Jul. 2014, 70 pages.

\* cited by examiner

S. R. Caskey, et al., *J. Am. Chem. Soc.* 2008, *130*, 10870

| Metal-organic framework | | Amount of adsorbed carbon dioxide (wt.%), 298 K | |
|---|---|---|---|
| | | 0.1 bar | 1.0 bar |
| Literature | [Mg$_2$(DOBDC)(DMF)$_2$] | 23.6 | 35.6 |
| | [Ni$_2$(DOBDC)(DMF)$_2$] | 11.6 | 25.6 |
| | [Co$_2$(DOBDC)(DMF)$_2$] | 11.7 | 30.6 |
| The present disclosure | [Mg$_2$(DOBDC)] | 30.0 | 41.8 |
| | [Ni$_2$(DOBDC)] | 21.7 | 37.3 |
| | [Co$_2$(DOBDC)] | 15.4 | 39.3 |

METAL-ORGANIC FRAMEWORKS AND PROCESS OF PREPARING THE SAME

CROSS-REFERENCE TO RELATED APPLICATIONS

This application claims, under 35 U.S.C. § 119, the priority of Korean Patent Application No. 10-2015-0143596 filed on Oct. 14, 2015 in the Korean Intellectual Property Office, the disclosure of which is incorporated herein by reference in its entirety.

TECHNICAL FIELD

The present disclosure relates to a metal-organic framework and a method for preparing the same.

BACKGROUND

A metal-organic framework (MOF) refers to a 3-dimensional hollow porous crystalline material prepared from self-assembly of a metal ion and an organic ligand (linker). Being a hollow 3-dimensional material, it is known to superior gas adsorption characteristics due to large surface area.

However, because it is practically impossible to completely remove a solvent such as dimethylformamide (DMF) bound to the metal ions inside pores, for example, by heat treatment, there has been limitation in remarkably increasing surface area and gas adsorption capacity.

In particular, although the solvent has to be removed completely to achieve high adsorption capacity for carbon dioxide and carbon monoxide bound to the metal ion at room temperature, the existing synthesis method is limited in this aspect.

REFERENCES CITED

Non-Patent Documents (1) Wendy L. Queen, Matthew R. Hudson, Eric D. Bloch, Jarad A. Mason, Miguel I. Gonzalez, Jason S. Lee, David Gygi, Joshua D. Howe, Kyuho Lee, Tamim A. Darwish, Michael James, Vanessa K. Peterson, Simon J. Teat, Berend Smit, Jeffrey B. Neaton, Jeffrey R. Long and Craig M. Brown, *Chem. Sc.*, 2014, 5, 4569-4581.
(2) S. R. Caskey, A. G. Wong-Foy and A. J. Matzger, *J. Am. Chem, Soc.*, 2008, 130, 10870-10871.
(3) P. D. C. Dietzel, R. Blom and H. Fjellvåg, *Eur. J. Inorg. Chem.*, 2008, 23, 3624-3632.
(4) D. Britt, H. Furukawa, B. Wang, T. G. Glover and O. M. Yaghi, *Proc. Natl. Acad. Sci. U.S.A.* 2009, 106, 20637-20640.

SUMMARY

The present disclosure aims at synthesizing a metal-organic framework with excellent crystallinity and increasing specific surface area and adsorption capacity for carbon dioxide and carbon monoxide by completely removing the solvent molecules bound to metal ions inside pores.

In an aspect, the present disclosure relates to a metal-organic framework represented by Chemical Formula 1:

$$[M_2(DOBDC)]. \qquad \text{[Chemical Formula 1]}$$

In another aspect, the present disclosure relates to a gas adsorbent containing a metal-organic framework according to an exemplary embodiment of the present disclosure.

In another aspect, the present disclosure relates to a method for preparing a metal-organic framework represented by Chemical Formula 4a, including:

(A) a step of preparing a solution containing (i) one or more metal precursor selected from $M^1A^1{}_{y1} \cdot x^1H_2O$, $M^2A^2{}_{y2} \cdot x^2H_2O$, $M^3A^3{}_{y3} \cdot x^3H_2O$, $M^4A^4{}_{y4} \cdot x^4H_2O$ and $M^5A^5{}_{y5} \cdot x^5H_2O$; (ii) 2,5-dihydroxy-1,4-benzenedicarboxylic acid or a derivative thereof; (iii) $S^1{}_{OH}$; (iv) an amine-based first additive; and (v) one or more second additive selected from diethylformamide, dimethylacetamide, benzylamine, diisopropylformamide and dimethylformamide and obtaining a metal-organic framework represented by Chemical Formula 4a by conducting a reaction:

$$[M^1{}_{n1}M^2{}_{n2}M^3{}_{n3}M^4{}_{n4}M^5{}_{R5}(DOBDC)(S^1{}_{OH})_2]. \qquad \text{[Chemical Formula 4a]}$$

In another aspect, the present disclosure relates to a method for preparing a metal-organic framework represented by Chemical Formula 4b, including:

(A) a step of preparing a solution containing (i) one or more metal precursor selected from $M^1A^1{}_{y1} \cdot x^1H_2O$, $M^2A^2{}_{y2} \cdot x^2H_2O$, $M^3A^3{}_{y3} \cdot x^3H_2O$, $M^4A^4{}_{y4} \cdot x^4H_2O$ and $M^5A^5{}_{y5} \cdot x^5H_2O$; (ii) 2,5-dihydroxy-1,4-benzenedicarboxylic acid or a derivative thereof; (iii) $S^1{}_{OH}$; (iv) an amine-based first additive; and (v) one or more second additive selected from diethylformamide (DEF), dimethylacetamide, benzylamine, diisopropylformamide and dimethylformamide and obtaining a metal-organic framework represented by Chemical Formula 4a by conducting a reaction:

$$[M^1{}_{n1}M^2{}_{n2}M^3{}_{n3}M^4{}_{n4}M^5{}_{n5}(DOBDC)(S^1{}_{OH})_2]; \text{ and} \qquad \text{[Chemical Formula 4a]}$$

(B) a step of obtaining a metal-organic framework represented by Chemical Formula 4b by contacting the metal-organic framework represented by Chemical Formula 4a with $S^2{}_{OH}$:

$$[M^1{}_{n1}M^2{}_{n2}M^3{}_{n3}M^4{}_{n4}M^5{}_{n5}(DOBDC)(S^2{}_{OH})_2]. \qquad \text{[Chemical Formula 4b]}$$

In another aspect, the present disclosure relates to a metal-organic framework represented by Chemical Formula 1e, including:

(A) a step of preparing a solution containing (i) one or more metal precursor selected from $M^1A^1{}_{y1} \cdot x^1H_2O$, $M^2A^2{}_{y2} \cdot x^2H_2O$, $M^3A^3{}_{y3} \cdot x^3H_2O$, $M^4A^4{}_{y4} \cdot x^4H_2O$ and $M^5A^5{}_{y5} \cdot x^5H_2O$; (ii) 2,5-dihydroxy-1,4-benzenedicarboxylic acid or a derivative thereof; (iii) $S^1{}_{OH}$; (iv) an amine-based first additive; and (v) one or more second additive selected from diethylformamide (DEF), dimethylacetamide, benzylamine and diisopropylformamide and obtaining a metal-organic framework represented by Chemical Formula 4a by conducting a reaction:

$$[M^1{}_{n1}M^2{}_{n2}M^3{}_{n3}M^4{}_{n4}M^5{}_{n5}(DOBDC)(S^1{}_{OH})_2]; \qquad \text{[Chemical Formula 4a]}$$

(B) a step of obtaining a metal-organic framework represented by Chemical Formula 4b by contacting the metal-organic framework represented by Chemical Formula 4a with $S^2{}_{OH}$:

$$[M^1{}_{n1}M^2{}_{n2}M^3{}_{n3}M^4{}_{n4}M^5{}_{n5}(DOBDC)(S^2{}_{OH})_2]; \text{ and} \qquad \text{[Chemical Formula 4b]}$$

(C) a step of obtaining a metal-organic framework represented by Chemical Formula 1e by drying the metal-organic framework represented by Chemical Formula 4b:

$$[M^1{}_{n1}M^2{}_{n2}M_{n3}M^4{}_{n4}M^5{}_{n5}(DOBDC)]. \qquad \text{[Chemical Formula 1e]}$$

In accordance with various exemplary embodiments of the present disclosure, a highly crystalline metal-organic framework having an organic solvent containing a hydroxyl group (—OH) bound to a metal on inside pores can be synthesized and the organic solvent bound to the metal ion can be completely removed through heat treatment without impairing the crystallinity.

Through this, a metal-organic framework having large specific surface area can be prepared and the prepared porous material exhibits high adsorption characteristics for carbon dioxide and carbon monoxide at room temperature.

DETAILED DESCRIPTION OF EMBODIMENTS

Figure 1:
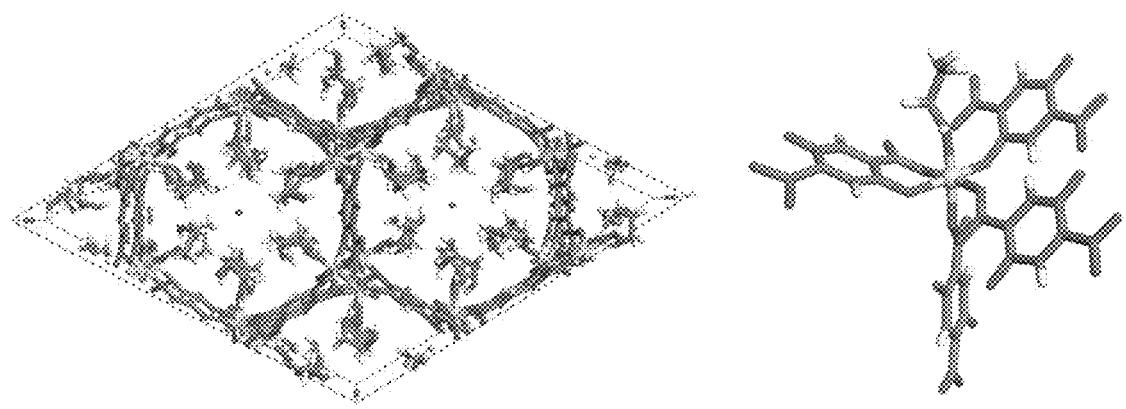
FIG. 1 shows the single crystal X-ray diffraction structure of a metal-organic framework synthesized using ethylene glycol having a hydrophilic OH functional group. It can be seen that ethylene glycol is bound to a metal displayed in green color.

Hereinafter, various aspects and exemplary embodiments of the present disclosure are described in more detail.

In an aspect, the present disclosure relates to a metal-organic framework represented by Chemical Formula 1.

                [Chemical Formula 1]

In Chemical Formula 1, M is one or more divalent metal and DOBDC is negatively charged, tetravalent 2,5-dioxido-1,4-benzenedicarboxylate.

In particular, the metal-organic framework (i) does not show peaks of a compound of Chemical Formula 2 in $^1$H-NMR analysis, (ii) does not show an amide peak in FT-IR analysis, (iii) shows less than 3% of weight change in TGA analysis when heated from 200° C. to 450° C., (iv) has a total pore volume of 0.70-1.00 cm$^3$/g, and (v) exhibits a BET surface area of up to 1,500-2,000 m$^2$/g:

In the present disclosure, examples of the divalent metal may include Ni$^{2+}$, Co$^{2+}$, Zn$^{2+}$, Mg$^{2+}$, Fe$^{2+}$, Cu$^{2+}$, Mn$^{2+}$, etc., although not being limited thereto. In the present disclosure, the divalent metal may include specifically Ni$^{2+}$, Co$_{2+}$, Zn$^{2+}$, Mg$^{2+}$, Fe$^{2+}$, Cu$^{2+}$ and Mn$^{2+}$. When these divalent metals are used, the metal-organic framework may have excellent crystallinity as compared to when other divalent metals are used.

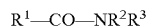                [Chemical Formula 2]

In Chemical Formula 2, each of R$^1$, R$^2$ and R$^3$, which are identical to or different from each other, is independently hydrogen or a C$_1$-C$_5$ alkyl group.

The compound of Chemical Formula 2 serves as a solvent for the metal-organic framework according to the present disclosure. Examples of the solvent of Chemical Formula 2 may include dimethylformamide, diethylformamide, dimethylacetamide (DMA), etc., although not being limited thereto.

According to the existing method, the metal-organic framework of Chemical Formula 1 can be prepared only by using the solvent of Chemical Formula 2 in excess. The solvent of Chemical Formula 2 is located inside a tunnel having a hexagonal cross section which is present inside the metal-organic framework. In the structure shown in FIG. 15, dimethylformamide bound to a metal displayed in green color corresponds to the ligand compound of Chemical Formula 2.

The specific amount of the solvent of Chemical Formula 2 used in the present disclosure is described in detail below when describing preparation methods according to various exemplary embodiments of the present disclosure.

Inside the prepared metal-organic framework, the solvent of Chemical Formula 2 is strongly bound to the divalent metal via a carbonyl group. Therefore, it is practically impossible to completely remove the solvent of Chemical Formula 2 from the metal-organic framework. As a result, a metal-organic framework [M$_2$(DOBDC)(R$^1$—CO—NR$^2$R$^3$)$_2$] with R$^1$—CO—NR$^2$R$^3$ bound to the compound of Chemical Formula 1, which is prepared according to the existing method, inevitably has the solvent of Chemical Formula 2 partially bound thereto without being completely removed.

In contrast, the metal-organic framework according to the present disclosure is prepared using an organic solvent containing a hydroxyl group such as ethylene glycol (EG) in excess, Since the organic solvent, which is relatively very easy to remove, is bound to the site where the solvent of Chemical Formula 2 is bound, the porous material of Chemical Formula 1 with no solvent bound to the metal-organic framework can be obtained in accordance with the method of the present disclosure.

As described above, the prepared metal-organic framework does not show an amide peak in FT-IR analysis and exhibits high heat resistance with less than 3% of weight change in TGA analysis when heated from 200° C. to 450° C.

In addition, it exhibits high porosity with a total pore volume of 0.70-1.00 cm$^3$/g and large surface area with a BET surface area of about 1,500-2,000 m$^2$/g. In particular, it exhibits remarkably improved carbon dioxide adsorption at room temperature with 30% (6.79 mmol/g) at 0.1 atm, 42 wt % (9.50 mmol/g) at 1 atm and up to 86 wt % (19.5 mmol/g) at saturation, as compared to the existing similar metal-organic framework.

In an exemplary embodiment, a metal-organic framework represented by any of Chemical Formulas 1a-1e is provided.

$$[M^1{}_{n1}(DOBDC)] \qquad \text{[Chemical Formula 1a]}$$

In Chemical Formula 1a, n1 is 2 and $M^1$ is a divalent metal.

$$[M^1{}_{n1}M^2{}_{n2}(DOBDC)] \qquad \text{[Chemical Formula 1b]}$$

In Chemical Formula 1 b, n1 and n2 real numbers which are equal to or greater than 0 and satisfy n1+n2=2; and each of $M^1$ and $M^2$, which are different from each other, is independently a divalent metal.

$$[M^1{}_{n1}M^2{}_{n2}M^3{}_{n3}(DOBDC)] \qquad \text{[Chemical Formula 1c]}$$

In Chemical Formula 1c, n1, n2 and n3 real numbers which are equal to or greater than 0 and satisfy n1+n2+n3=2; and each of $M^1$, $M^2$ and $M^3$, which are different from each other, is independently a divalent metal.

$$[M^1{}_{n1}M^3{}_{n2}M^3{}_{n3}M^4{}_{n4}(DOBDC)] \qquad \text{[Chemical Formula 1d]}$$

In Chemical Formula 1d, n1, n2, n3 and n4 real numbers which are equal to or greater than 0 and satisfy n1+n2+n3+n4=2; and each of $M^1$, $M^2$, $M^3$ and $M^4$, which are different from each other, is independently a divalent metal.

$$[M^1{}_{n1}M^2{}_{n2}M^3{}_{n3}M^4{}_{n4}M^5{}_{n5}(DOBDC)] \qquad \text{[Chemical Formula 1e]}$$

In Chemical Formula 1e, n1, n2, n3, n4 and n5 real numbers which are equal to or greater than 0 and satisfy n1+n2+n3+n4+n5=2; and each of $M^1$, $M^2$, $M^3$, $M^4$ and $M^5$, which are different from each other, is independently a divalent metal.

In another exemplary embodiment, a metal-organic framework represented by Chemical Formula 3 is provided.

$$[M_2(DOBDC)(S_{OH})_2] \qquad \text{[Chemical Formula 3]}$$

In Chemical Formula 1, M is one or ore divalent metal; DOBDC is negatively charged, tetravalent 2,5-dioxido-1,4-benzenedicarboxylate, and $S_{OH}$ is an organic solvent containing a hydroxyl group.

In the present disclosure, examples of the organic solvent containing a hydroxyl group may include ethylene glycol (EG), methanol (MeOH), ethanol (EtOH), glycerol (Gly), isopropyl alcohol (IPA), 1-propanol, propylene glycol, etc., although not being limited thereto.

In particular, the solvent containing a hydroxyl group may contain specifically one or more hydroxyl group and one of them may be bound to the metal so that it can be easily exchanged with another solvent such as ethanol or methanol through post-treatment.

More specifically, the solvent containing a hydroxyl group may contain two or more hydroxyl groups. One of the hydroxyl groups may be bound to the metal and the other hydroxyl group(s) may protrude toward the pores to form a hydrophilic surface so that exchange with another solvent such as ethanol or methanol can be easily achieved under a milder condition through post-treatment with a higher conversion ratio.

In another exemplary embodiment, a metal-organic framework represented by any of Chemical Formulas 3a-3e is provided.

$$[M^1{}_{n1}(DOBDC)(S_{OH})_2] \qquad \text{[Chemical Formula 3a]}$$

In Chemical Formula 3a, n1 is 2 and $M^1$ is a divalent metal.

$$[M^1{}_{n1}M^2{}_{n2}(DOBDC)(S_{OH})_2] \qquad \text{[Chemical Formula 3b]}$$

In Chemical Formula 3b, n1 and n2 are real numbers which are equal to or greater than 0 and satisfy n1+n2=2; and each of $M^1$ and $M^2$, which are different from each other, is independently a divalent metal.

$$[M^1{}_{n1}M^2{}_{n2}M^3{}_{n3}(DOBDC)(S_{OH})_2] \qquad \text{[Chemical Formula 3c]}$$

In Chemical Formula 3c, n1, n2 and n3 are real numbers which are equal to or greater than 0 and satisfy n1+n2+n3=2; and each of $M^1$, $M^2$ and $M^3$, which are different from each other, is independently a divalent metal.

$$[M^1{}_{n1}M^2{}_{n2}M^3{}_{n3}M^4{}_{n4}(DOBDC)(S_{OH})_2] \qquad \text{[Chemical Formula 3d]}$$

In Chemical Formula 3d, n1, n2, n3 and n4 are real numbers which are equal to or greater than 0 and satisfy n1+n2+n3+n4=2; and each of $M^1$, $M^2$, $M^3$ and $M^4$, which are different from each other, is independently a divalent metal.

$$[M^1{}_{n1}M^2{}_{n2}M^3{}_{n3}M^4{}_{n4}M^5{}_{n5}(DOBDC)(S_{OH})_2] \qquad \text{[Chemical Formula 3e]}$$

In Chemical Formula 3e, n1, n2, n3, n4 and n5 are real numbers which are equal to or greater than 0 and satisfy n1+n2+n3+n4+n5=2; and each of $M^1$, $M^2$, $M^3$, $M^4$ and $M^5$, which are different from each other, is independently a divalent metal.

In another aspect, the present disclosure relates to a gas adsorbent containing the metal-organic framework according to various exemplary embodiments of the present disclosure. A gas adsorbed by the gas adsorbent is carbon monoxide, carbon dioxide or a mixture thereof.

In another aspect, the present disclosure relates to a method for preparing a metal-organic framework represented by Chemical Formula 4a, including:

(A) a step of preparing a solution containing (i) one or more metal precursor selected from $M^1A^1{}_{y1} \cdot x^1H_2O$, $M^2A^2{}_{y2} \cdot x^2H_2O$, $M^3A^3{}_{y3} \cdot x^3H_2O$, $M^4A^4{}_{y4} \cdot x^4H_2O$ and $M^5A^5{}_{y5} \cdot x^5H_2O$; (ii) 2,5-dihydroxy-1,4-benzenedicarboxylic acid or a derivative thereof; (iii) $S^1{}_{OH}$; (iv) an amine-based first additive; and (v) one or more second additive selected from diethylformamide, dimethylacetamide, benzylamine, diisopropylformamide and dimethylformamide and obtaining a metal-organic framework represented by Chemical Formula 4a by conducting a reaction:

$$[M^1{}_{n1}M^2{}_{n2}M^3{}_{n3}M^4{}_{n4}M^5{}_{R5}(DOBDC)(S^1{}_{OH})_2] \qquad \text{[Chemical Formula 4a]}$$

wherein n1, n2, n3, n4 and n5 are real numbers which are equal to or greater than 0 and satisfy n1+n2+n3+n4+n5=2;

each of $M^1$, $M^2$, $M^3$, $M^4$ and $M^5$, which are different from each other, is independently a divalent metal;

each of $A^1$, $A^2$, $A^3$, $A^4$ and $A^5$, which are identical to or different from each other, is independently a monovalent anion selected from $NO_3^-$, $Cl^-$, $ClO_4^-$, $OH^-$ and $CH_3CO_2^-$ or a divalent anion selected from $ClO_4^{2-}$, $SO_4^{2-}$ and $CO_3^{2-}$;

each of $x^1$, $x^2$, $x^3$, $x^4$ and $x^5$, which are identical to or different from each other, is independently an integer from 1 to 50; and if $A^1$ is a monovalent anion or a divalent anion then y1 is 2 or 1, respectively, if $A^2$ is a monovalent anion or a divalent anion then y2 is 2 or 1, respectively, if $A^3$ is a monovalent anion or a divalent anion then y3 is 2 or 1, respectively, if $A^4$ is a monovalent anion or a divalent anion then y4 is 2 or 1, respectively, and if $A^5$ is a monovalent anion or a divalent anion then y5 is 2 or 1, respectively.

The derivative of 2,5-dihydroxy-1,4-benzenedicarboxylic acid is one or more selected from a dehydrogenated ion or salt of 2,5-dihydroxy-1,4-benzenedicarboxylic acid;

$S^1_{OH}$ is an organic solvent containing a hydroxyl group.

It is important that (i) $S^1_{OH}$ is used in an amount of 50-95 vol % based on the total volume of the solution, (ii) the second additive is used in an amount of 5-50% based on the total volume of the solution and (iii) in an amount of 1-100% based on the volume of $S^1_{OH}$.

It was found out that the effect desired by the present disclosure, i.e., the metal-organic framework of Chemical Formula 1 which (i) does not show peaks of a compound of Chemical Formula 2 in $^1$H-NMR analysis, (ii) does not show an amide peak in FT-IR analysis, (iii) shows less than 3% of weight change in TGA analysis when heated from 200° C. to 450° C., (iv) has a total pore volume of 0.70-1.00 cm$^3$/g, and (v) exhibits a BET surface area of up to 1,500-2,000 m$^2$/g, cannot be obtained when the amounts of $S^1_{OH}$ and the second additive are outside the above-described ranges. Accordingly, it is of great importance to keep the above-described ranges.

In the present disclosure, the amine-based first additive may be an amine-based organic base selected from an aromatic amine, a cyclic amine, an alicyclic amine and a linear aliphatic amine. Examples of the aromatic amine may include p-phenylenediamine, m-phenylenediamine, aniline, 3,5-diaminobenzoic acid, melamine, etc. Examples of the cyclic amine may include cyclohexylamine, cyclopentylamine, norbornene amine and adamantanamine, Examples of the cyclic amine may include pyridine, piperidine and an azole-based compound. Examples of the azole-based compound may include pyrrole, imidazole, pyrazole, triazole, etc. And, examples of the linear aliphatic amine may include an amine compound having 1-5 amine group(s) attached to a $C_1$-$C_7$ aliphatic hydrocarbon.

In particular, the first additive may be an organic base which dehydrogenates DOBDC to DOBDC$^{4-}$ and may be selected from, specifically, melamine, aniline and methylamine. In particular, when melamine is used, a product with larger surface area can be obtained as compared to when other candidate materials of the first additive described above are used.

Specifically, the amine-based first additive may be used in an amount of 1-50 wt % based on the weight of the metal precursor and in an amount of 5-200 wt % based on the weight of the 2,5-dihydroxy-1,4-benzenedicarboxylic acid or a derivative thereof. When the amount of the amine-based first additive is less than the lowest limit, the yield of the metal-organic framework may decrease drastically. And, when the amount of the amine-based first additive exceeds the highest limit, metal-organic framework may not be formed due to binding with the metal.

Specifically, the 2,5-dihydroxy-1,4-benzenedicarboxylic acid or a derivative thereof may be used in an amount of 10-200 wt % based on the weight of the metal precursor.

The second additive serves as a solvent for dissolving DOBDC. In particular, when dimethylformamide is used, the product can be obtained with a higher yield as compared to when other candidate materials of the second additive described above are used.

In particular, when dimethylformamide is used among the second additives described in the present disclosure, it was found out that, if it is used in an amount outside the range of 5-50% based on the total volume of the solution or outside the range of 1-100% based on the volume of $S^1_{OH}$, it is trapped inside the metal-organic framework in the form of a ligand represented by Chemical Formula 2, thereby greatly decreasing gas adsorption ability.

In another aspect, the present disclosure elates to a method for preparing a metal-organic framework represented by Chemical Formula 4b, including:

(A) preparing a solution containing (i) one or more metal precursor selected from $M^1A^1_{y1} \cdot x^1H_2O$, $M^2A^2_{y2} \cdot x^2H_2O$, $M^3A^3_{y3} \cdot x^3H_2O$, $M^4A^4_{y4} \cdot x^4H_2O$ and $M^5A^5_{y5} \cdot x^5H_2O$; (ii) 2,5-dihydroxy-1,4-benzenedicarboxylic acid or a derivative thereof; (iii) $S^1_{OH}$; (iv) an amine-based first additive; and (v) one or more second additive selected from diethylformamide, dimethylacetamide, benzylamine, diisopropylformamide and dimethylformamide and obtaining a metal-organic framework represented by Chemical Formula 4a by conducting a reaction:

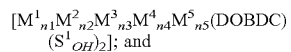
$[M^1_{n1}M^2_{n2}M^3_{n3}M^4_{n4}M^5_{n5}(DOBDC)(S^1_{OH})_2]$; and     [Chemical Formula 4a]

(B) obtaining a metal-organic framework represented by Chemical Formula 4b by contacting the metal-organic framework represented by Chemical Formula 4a with $S^2_{OH}$:

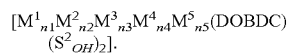
$[M^1_{n1}M^2_{n2}M^3_{n3}M^4_{n4}M^5_{n5}(DOBDC)(S^2_{OH})_2]$.     [Chemical Formula 4b]

wherein n1, n2, n3, n4 and n5 are real numbers which are equal to or greater than 0 and satisfy n1+n2+n3+n4+n5=2;

each of $M^1$, $M^2$, $M^3$, $M^4$ and $M^5$, which are different from each other, is independently a divalent metal;

each of $A^1$, $A^2$, $A^3$, $A^4$ and $A^5$, which are identical to or different from each other, is independently a monovalent anion selected from $NO_3^-$, $Cl^-$, $ClO_4^-$, $OH^-$ and $CH_3CO_2^-$ or a divalent anion selected from $ClO_4^{2-}$, $SO_4^{2-}$ and $CO_3^{2-}$;

each of $x^1$, $x^2$, $x^3$, $x^4$ and $x^5$, which are identical to or different from each other, is independently an integer from 1 to 50; and if $A^1$ is a monovalent anion or a divalent anion then y1 is 2 or 1, respectively, if $A^2$ is a monovalent anion or a divalent anion then y2 is 2 or 1, respectively, if $A^3$ is a monovalent anion or a divalent anion then y3 is 2 or 1, respectively, if $A^4$ is a monovalent anion or a divalent anion then y4 is 2 or 1, respectively, and if $A^5$ is a monovalent anion or a divalent anion then y5 is 2 or 1, respectively.

The derivative of 2,5-dihydroxy-1,4-benzenedicarboxylic acid is one or more selected from a dehydrogenated ion or salt of 2,5-dihydroxy-1,4-benzenedicarboxylic acid.

$S^1_{OH}$ is a first organic solvent containing a hydroxyl group and $S^2_{OH}$ is a second organic solvent containing a hydroxyl group.

In the present disclosure, examples of the organic solvent containing a hydroxyl group may include ethylene glycol (EG), methanol (MeOH), ethanol (EtOH), glycerol (Gly), isopropyl alcohol (IPA), 1-propanol, propylene glycol, etc., although not being limited thereto.

In particular, as the organic solvents containing a hydroxyl group, the first organic solvent and the second organic solvent may be used distinctively and sequentially. It is because it is easier to prepare a metal-organic framework not containing a hydroxyl group to prepare a metal-organic framework using the first organic solvent with a high boiling point and then to exchange it with the second organic solvent with a low boiling point.

In the present disclosure, the first organic solvent containing a hydroxyl group may be a ligand containing a hydroxyl group and having a relatively high boiling point. Specific examples may include ethylene glycol, glycerol, propylene glycol, 1-propanol, etc., although not being limited thereto.

And, the second organic solvent containing a hydroxyl group may be a solvent containing a hydroxyl group and having a relatively low boiling point. Specific examples may include methanol, ethanol, isopropyl alcohol, etc., although not being limited thereto.

In another aspect, the present disclosure relates to a method for preparing a metal-organic framework represented by Chemical Formula 1e, including:

(A) preparing a solution containing (i) one or more metal precursor selected from $M^1A^1_{y1} \cdot x^1H_2O$, $M^2A^2_{y2} \cdot x^2H_2O$, $M^3A^3_{y3} \cdot x^3H_2O$, $M^4A^4_{y4} \cdot x^4H_2O$ and $M^5A^5_{y5} \cdot x^5H_2O$; (ii) 2,5-dihydroxy-1,4-benzenedicarboxylic acid or a derivative thereof; (iii) $S^1_{OH}$; (iv) an amine-based first additive; and (v) one or more second additive selected from diethylformamide, dimethylacetamide, benzylamine, diisopropylformamide and dimethylformamide and obtaining a metal-organic framework represented by Chemical Formula 4a by conducting a reaction:

[Chemical Formula 4a]

(B) obtaining a metal-organic framework represented by Chemical Formula 4b by contacting the metal-organic framework represented by Chemical Formula 4a with $S^2_{OH}$;

[Chemical Formula 4b]; and (C) obtaining a metal-organic framework represented by Chemical Formula 1e by drying the metal-organic framework represented by Chemical Formula 4b:

[Chemical Formula 1e]

wherein n1, n2, n3, n4 and n5 are real numbers which are equal to or greater than 0 and satisfy n1+n2+n3+n4+n5=2;

each of $M^1$, $M^2$, $M^3$, $M^4$ and $M^5$, which are different from each other, is independently a divalent metal;

each of $A^1$, $A^2$, $A^3$, $A^4$ and $A^5$, which are identical to or different from each other, is independently a monovalent anion selected from $NO_3^-$, $Cl^-$, $ClO_4^-$, $OH^-$ and $CH_3CO_2^-$ or a divalent anion selected from $ClO_4^{2-}$, $SO_4^{2-}$ and $CO_3^{2-}$;

each of $x^1$, $x^2$, $x^3$, $x^4$ and $x^5$, which are identical to or different from each other, is independently an integer from 1 to 50; and if $A^1$ is a monovalent anion or a divalent anion then y1 is 2 or 1, respectively, if $A^2$ is a monovalent anion or a divalent anion then y2 is 2 or 1, respectively, if $A^3$ is a monovalent anion or a divalent anion then y3 is 2 or 1, respectively, if $A^4$ is a monovalent anion or a divalent anion then y4 is 2 or 1, respectively, and if $A^5$ is a monovalent anion or a divalent anion then y5 is 2 or 1, respectively.

The derivative of 2,5-dihydroxy-1,4-benzenedicarboxylic acid is one or more selected from a dehydrogenated ion or salt of 2,5-dihydroxy-1,4-benzenedicarboxylic acid.

$S^1_{OH}$ is a first organic solvent containing a hydroxyl group and $S^2_{OH}$ is a second organic solvent containing a hydroxyl group.

EXAMPLES

Hereinafter, the present disclosure will be described in detail through examples. However, the scope and content of the present disclosure are not limited by the following examples. Also, it will be apparent that those of ordinary skill in the art that can easily carry out the present disclosure specific experimental results of which are not described based on the description of the present disclosure including the following examples. It is also obvious that such changes and modifications fall in the scope of the attached claims.

Only the representative experimental results of the examples and comparative examples are described below.

Example 1

Figure 2:
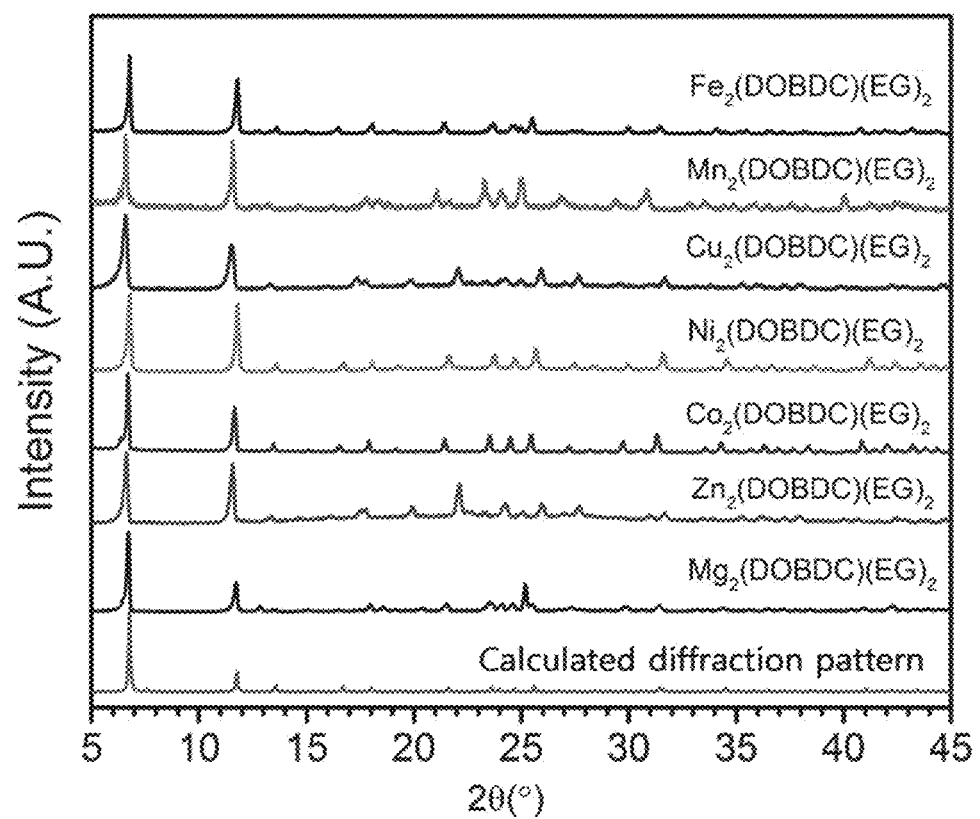
FIG. 2 shows the powder X-ray diffraction data of a metal-organic framework synthesized using ethylene glycol having a hydrophilic OH functional group.
Figure 3:
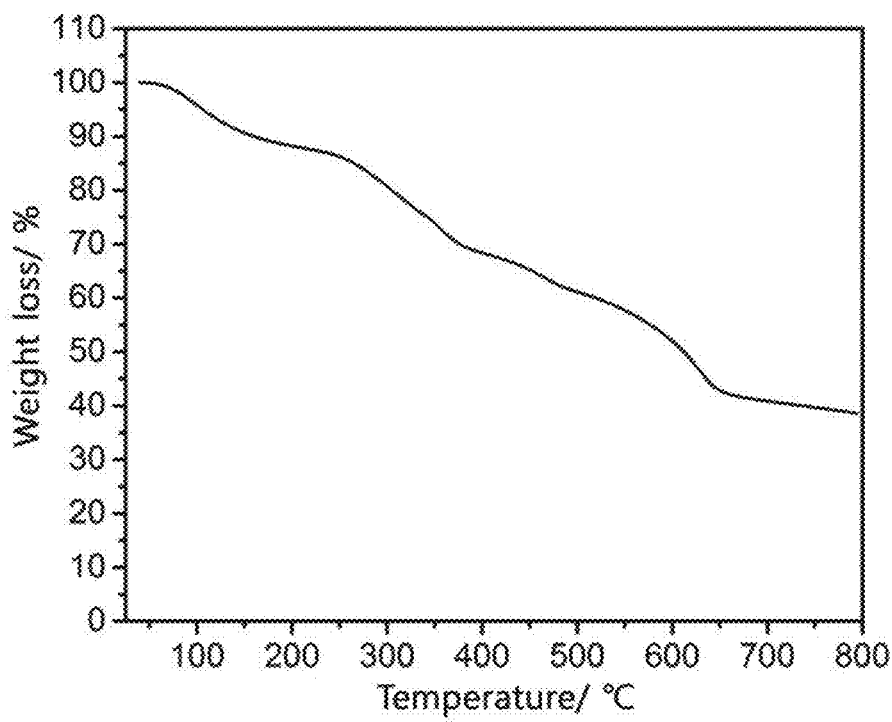
FIG. 3 shows the thermogravimetric analysis (TGA) data of [$Mg_2$(DOBDC)].

116 mg of 2,5-dihydroxy-1,4-benzenedicarboxylic acid (2,5-DOBDC), 100 mg of melamine, 10 mL of ethylene glycol and 2 mL of dimethylformamide were used per 600 mg of $Mg(NO_3)_2 \cdot 6H_2O$. Reaction temperature was 130° C. and reaction time was 24 hours. The single crystal X-ray diffraction structure of the prepared $Mg_2(DOBDC)(EG)_2$ is shown in FIG. 1. The single crystal parameters were: trigonal, R-3, a=25.951(4) Å, b=25.951(4) Å, c=13.632(3), α=90, β=90, γ=120, V=7951(2) Å$^3$, Z=18, T=100(2) K, $d_{calc}$=1.635 g/cm$^3$, $R_1$=0.0879 (I>2σ(I)), $wR_2$=0.2552 (all data), GOF=1.060. The powder X-ray diffraction data are shown in FIG. 2. The thermogravimetric analysis (TGA) data are shown in FIG.

Example 2

Figure 4:
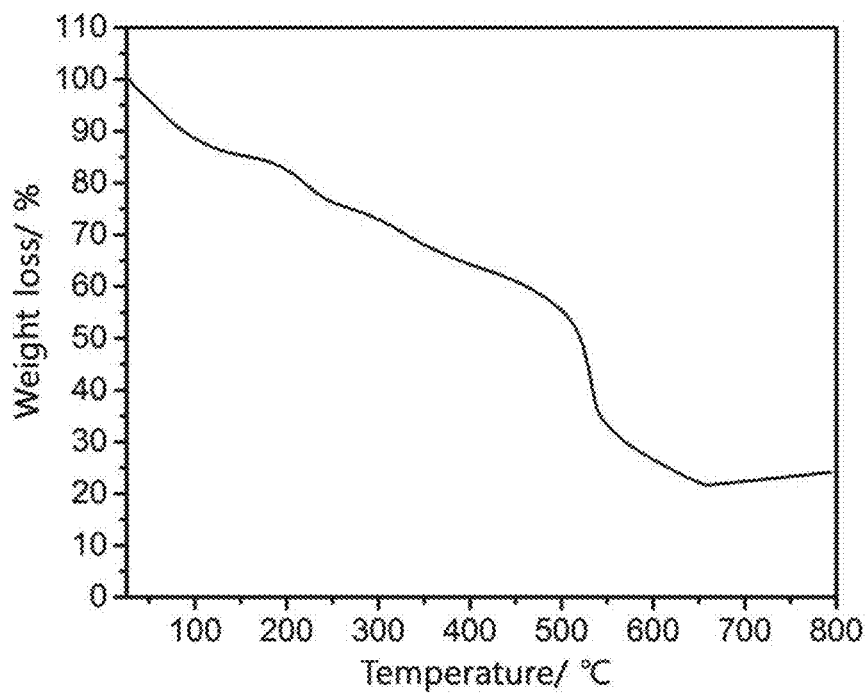
FIG. 4 shows the thermogravimetric analysis (TGA) data of [$Co_2$(DOBDC)].

166 mg of 2,5-dihydroxy-1,4-benzenedicarboxylic acid (2,5-DOBDC), 100 mg of melamine, 10 mL of ethylene glycol and 2 mL of dimethylformamide were used per 600 mg of $Co(NO_3)_2 \cdot 6H_2O$. Reaction temperature was 130° C. and reaction time was 24 hours. The single crystal X-ray diffraction structure of the prepared $Co_2(DOBDC)(EG)_2$ is shown in FIG. 1. The single crystal parameters were: trigonal, R-3, a=26.070(4) Å, b=26.070(4) Å, c=13.521(3), α=90, β=90, γ=120, V=7958(2) Å$^3$, Z=18, T=100(2) K, $d_{calc}$=1.894 g/cm$^3$, $R_1$=0.0581 (I>2σ(I)), $wR_2$=0.1624 (all data), GOF=1.093. The powder X-ray diffraction data are shown in FIG. 2. The thermogravimetric analysis (TGA) data are shown in FIG. 4.

Example 3

Figure 5:
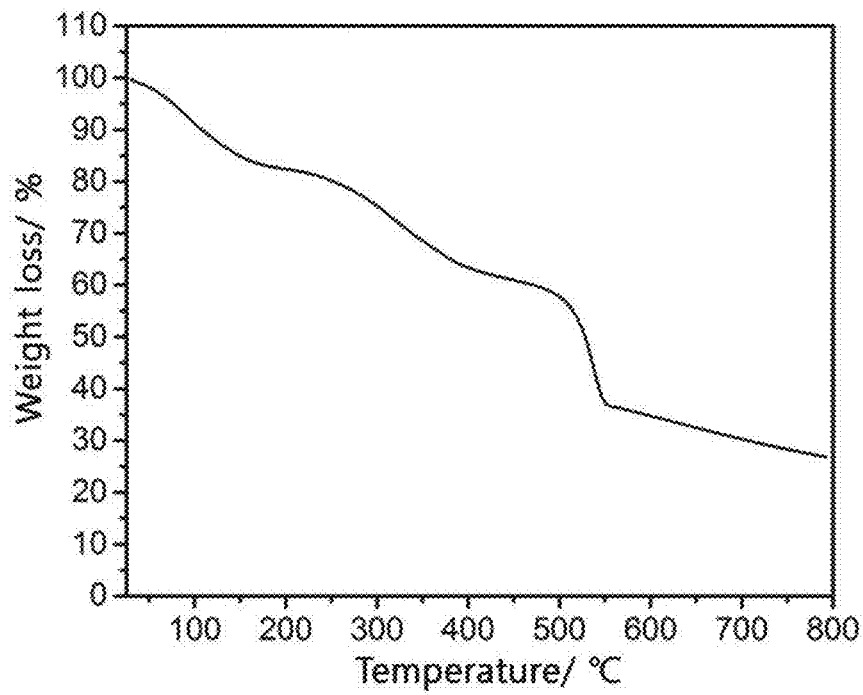
FIG. 5 shows the thermogravimetric analysis (TGA) data of [$Ni_2$(DOBDC)].

116 mg of 2,5-dihydroxy-1,4-benzenedicarboxylic acid (2,5-DOBDC), 100 mg of melamine, 10 mL of ethylene glycol and 2 mL of dimethylformamide were used per 600 mg of $Ni(NO_3)_2 \cdot 6H_2O$. Reaction temperature was 130° C. and reaction time was reaction time 24 hours. The single crystal X-ray diffraction structure of the prepared $Ni_2(DOBDC)(EG)_2$ is shown in FIG. 1. The single crystal parameters were: trigonal, R-3, a=26.137(4) Å, b=26.137(4) Å, c=13.337(3), α=90, β=90, γ=120, V=7890(2) Å$^3$, Z=18, T=100(2) K, $d_{calc}$=1.940 g/cm$^3$, $R_1$=0.1050 (I>2σ(I)), $wR_2$=0.2607 (all data), GOF=1.260. The powder X-ray diffraction data are shown in FIG. 2. The thermogravimetric analysis (TGA) data are shown in FIG. 5.

Example 4

Figure 6:
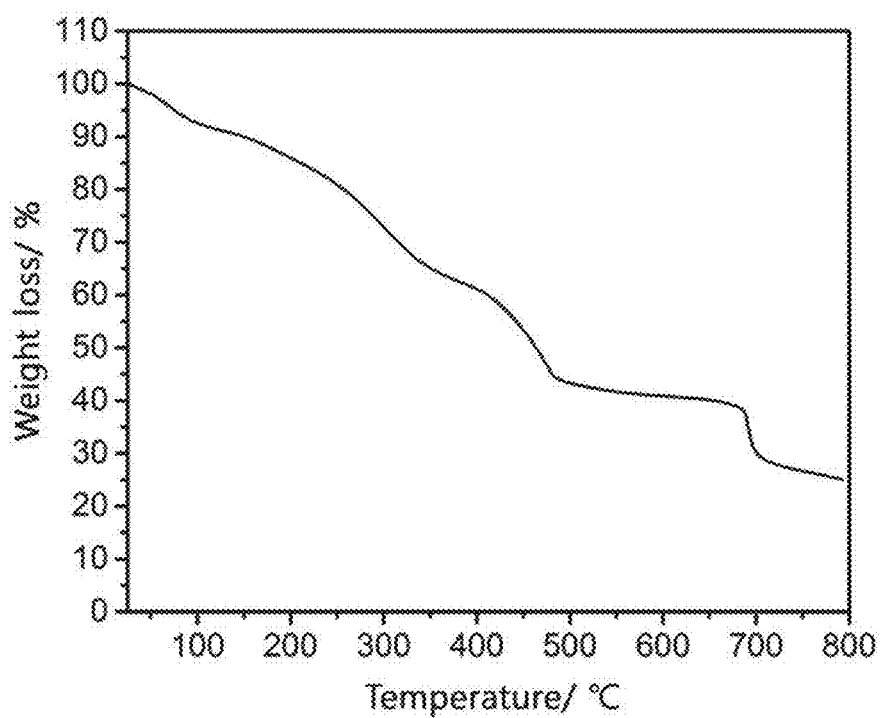
FIG. 6 shows the thermogravimetric analysis (TGA) data of [$Fe_2$(DOBDC)].

600 mg of 2,5-dihydroxy-1,4-benzenedicarboxylic acid (2,5-DOBDC), 100 mg of melamine, 10 mL of ethylene glycol and 2 mL of dimethylformamide were used per 600 mg of $FeCl_2 \cdot 4H_2O$. Reaction temperature was 130° C. and reaction time was 24 hours. The single crystal X-ray diffraction structure of the prepared $Fe_2(DOBDC)(EG)_2$ is shown in FIG. 1. The powder X-ray diffraction data are shown in FIG. 2. The thermogravimetric analysis (TGA) data are shown in FIG. 6.

Example 5

166 mg of 2,5-dihydroxy-1,4-benzenedicarboxylic acid (2,5-DOBDC), 100 mg of melamine, 10 mL of ethylene glycol and 2 mL of dimethylformamide were used per 600 mg of $MnCl_2$. Reaction temperature was 130° C. and reaction time was 24 hours. The single crystal X-ray diffraction structure of the prepared $Mn_2(DOBDC)(EG)_2$ is shown in FIG. 1. The powder X-ray diffraction data are shown in FIG. 2.

Example 6

300 mg of 2,5-dihydroxy-1,4-benzenedicarboxylic acid (2,5-DOBDC), 100 mg of melamine, 10 mL of ethylene glycol and 2 mL of dimethylformamide were used per 600 mg of $Cu(NO_3)_2 \cdot 3H_2O$. Reaction temperature was 130° C. and reaction time was 24 hours. The single crystal X-ray diffraction structure of the prepared $Cu_2(DOBDC)(EG)_2$ is shown in FIG. 1. The powder X-ray diffraction data are shown in FIG. 2.

Example 7

166 mg of 2,5-dihydroxy-1,4-benzenedicarboxylic acid (2,5-DOBDC), 100 mg of melamine, 10 mL of ethylene glycol and 2 mL of dimethylformamide were used per 600 mg of $ZnCl_2$. Reaction temperature was 130° C. and reaction time was 24 hours. The single crystal X-ray diffraction structure of the prepared $Zn_2(DOBDC)(EG)_2$ is shown in FIG. 1. The powder X-ray diffraction data are shown in FIG. 2.

Example 8

Figure 7:
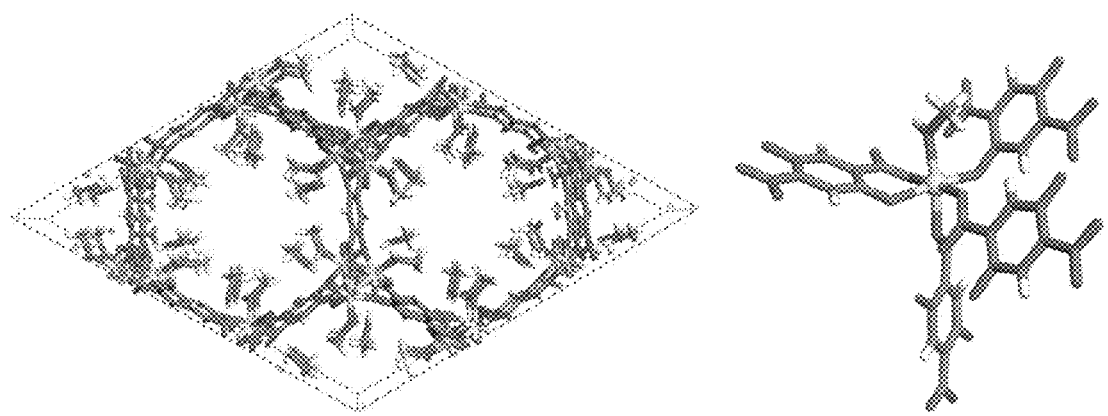
FIG. 7 shows the single crystal X-ray diffraction structure of a metal-organic framework synthesized by exchanging ethylene glycol bound to a metal with methanol. It can be seen that methanol is bound to a metal displayed in green color.
Figure 8:
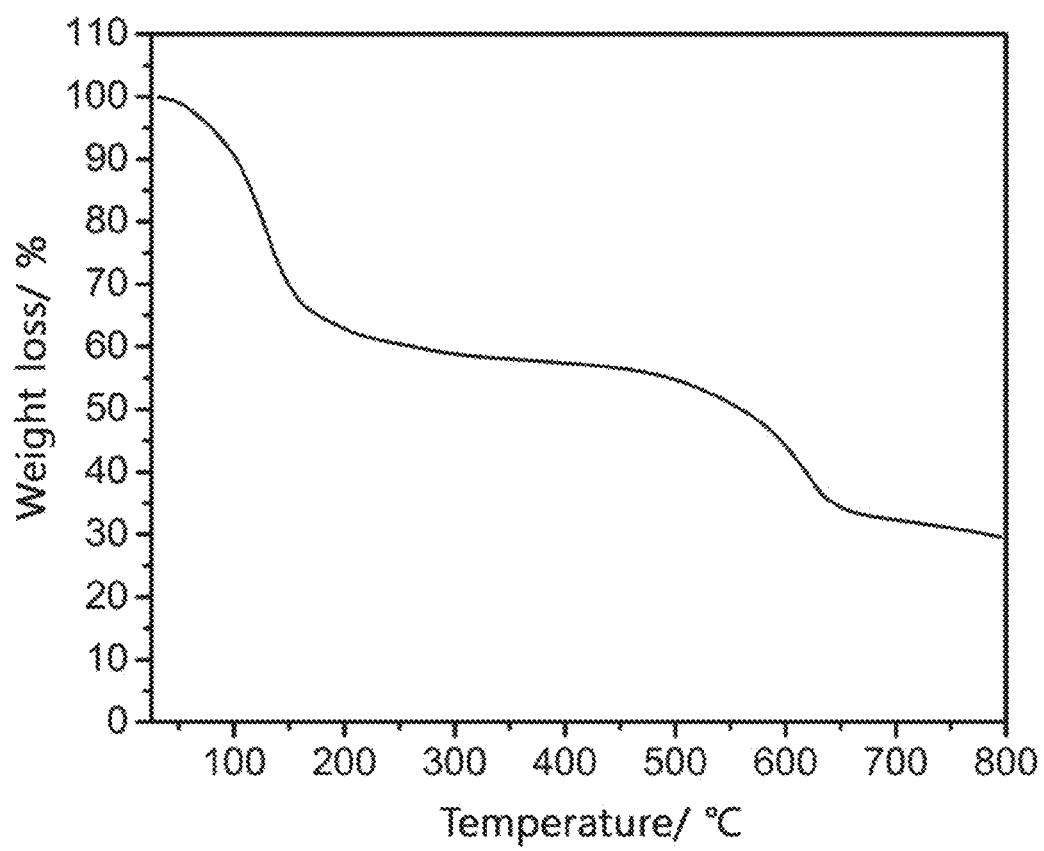
FIG. 8 shows the thermogravimetric analysis (TGA) data of [$Mg_2$(DOBDC)(MeOH)$_2$].

After adding $Mg_2(DOBDC)(EG)_2$, $Co_2(DOBDC)(EG)_2$, $Ni_2(DOBDC)(EG)_2$, $Fe_2(DOBDC)(EG)_2$, $Mn_2(DOBDC)(EG)_2$, $Cu_2(DOBDC)(EG)_2$ and $Zn_2(DOBDC)(EG)_2$ prepared in Examples 1-7 to 15 mL of methanol, ethylene glycol was completely exchanged with methanol by heating at 200° C. for 4 days. The single crystal X-ray diffraction structures of the prepared $Mg_2(DOBDC)(MeOH)_2$, $Co_2(DOBDC)(MeOH)_2$, $Ni_2(DOBDC)(MeOH)_2$, $Fe_2(DOBDC)(MeOH)_2$, $Mn_2(DOBDC)(MeOH)_2$, $Cu_2(DOBDC)(MeOH)_2$ and $Zn_2(DOBDC)(MeOH)_2$ are shown in FIG. 7. The single crystal parameters for $Mg_2(DOBDC)(EG)_2$ were: trigonal, R-3, a=26.023(4) Å, b=26.023(4) Å, c=13.305(3), α=90, β=90, γ=120, V=7803(2) Å$^3$, Z=18, T=100(2) K, $d_{calc}$=1.421 g/cm$^3$, $R_1$=0.0419 (I>2σ(I)), wR$_2$=0.2143 (all data), GOF=0.995. The thermogravimetric analysis (TGA) data are shown in FIG. 8.

Example 9

Figure 9:
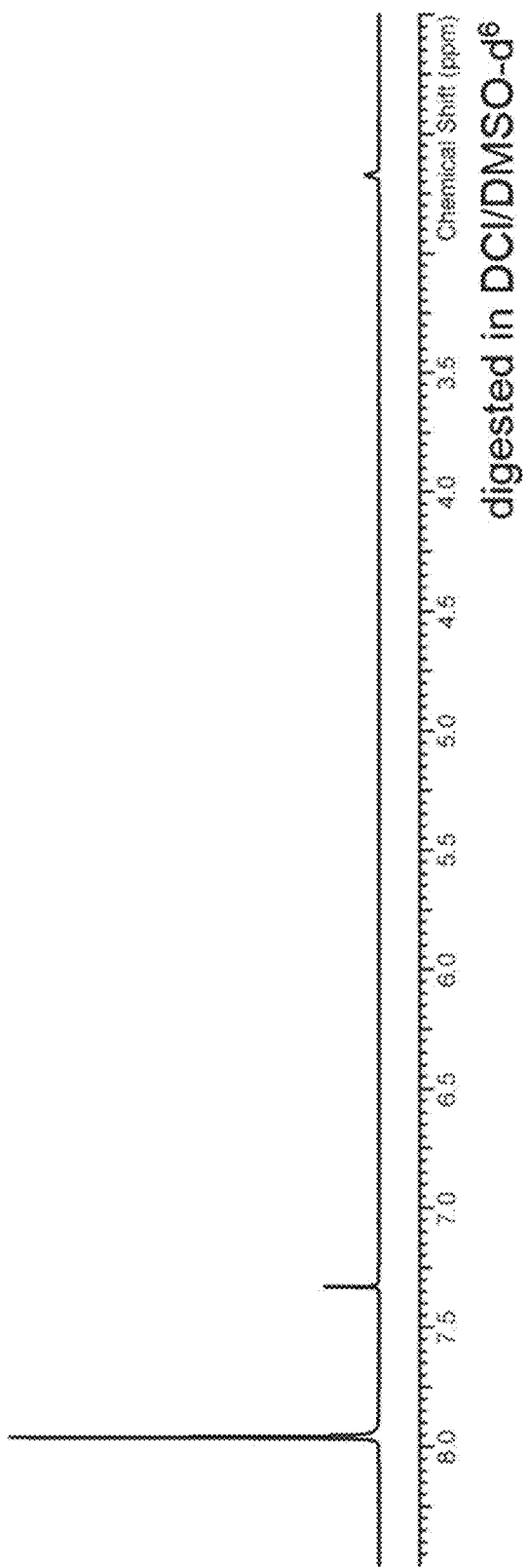
FIG. 9 shows the $^1$H-NMR data of [$Mg_2$(DOBDC)].
Figure 10:
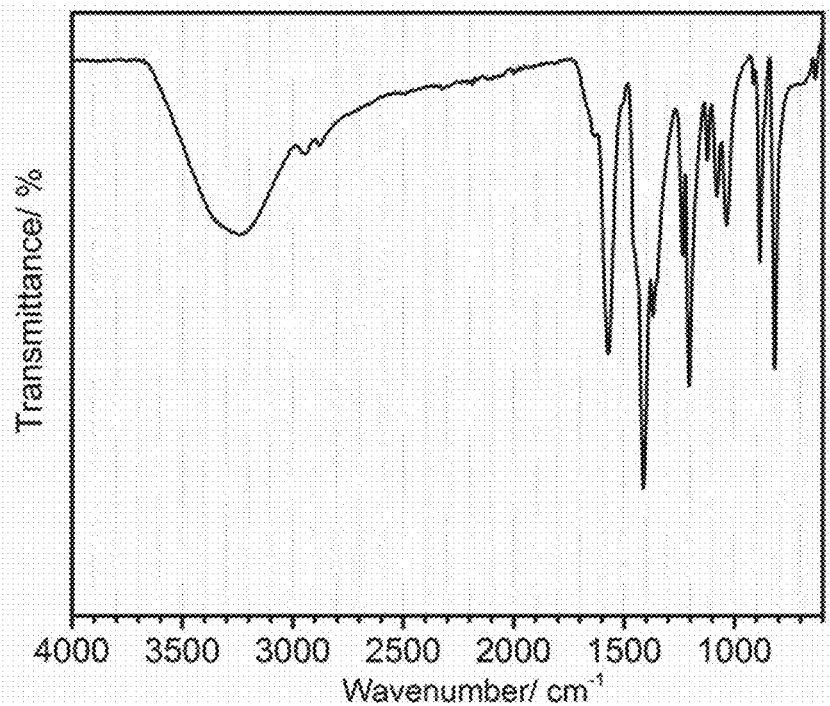
FIG. 10 shows the FT-IR spectrum of [[$Mg_2$(DOBDC)].
Figure 11:
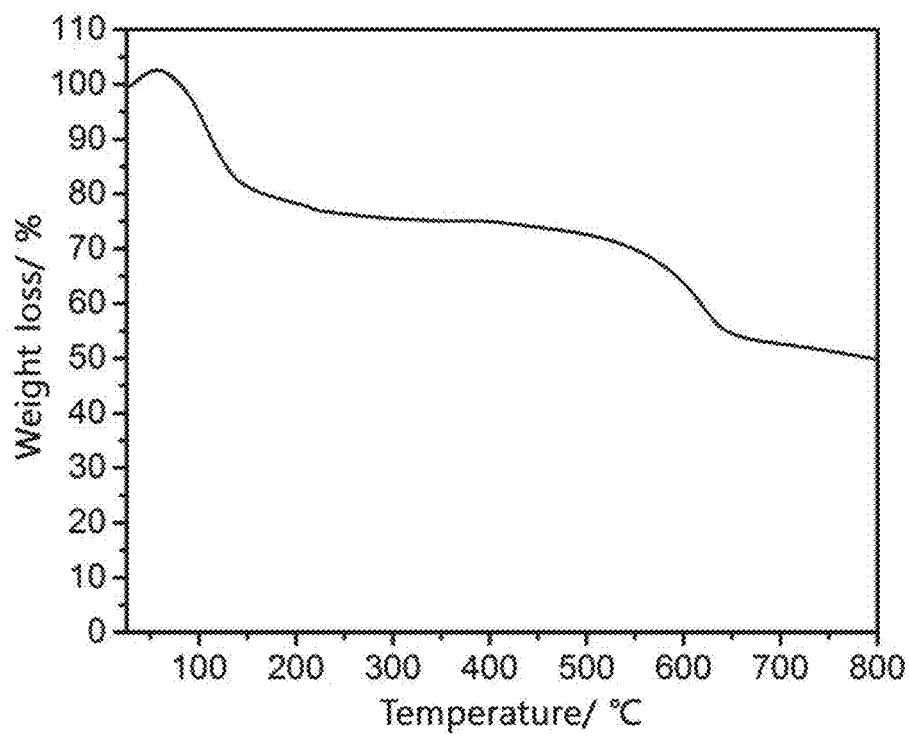
FIG. 11 shows the thermogravimetric analysis (TGA) data of [$Mg_2$(DOBDC)].
Figure 12:
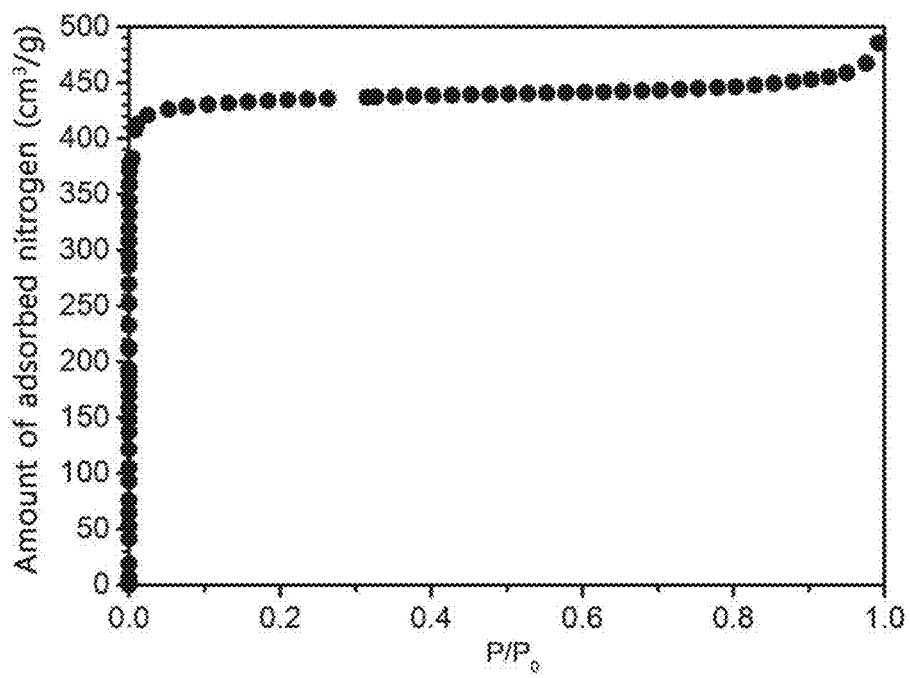
FIG. 12 shows the nitrogen adsorption isotherm of [$Mg_2$(DOBDC)] at 77 K after pretreatment.

After completely removing methanol was from $Mg_2(DOBDC)(MeOH)_2$, $Co_2(DOBDC)(MeOH)_2$, $Ni_2(DOBDC)(MeOH)_2$, $Fe_2(DOBDC)(MeOH)_2$, $Mn_2(DOBDC)(MeOH)_2$, $Cu_2(DOBDC)(MeOH)_2$ and $Zn_2(DOBDC)(MeOH)_2$ by heating at 250° C. for 1-7 days under a vacuum atmosphere, the structure of the $[M_2(DOBDC)]$ (M=Mg, Co, Ni, Fe, Mn, Cu, Zn) was analyzed. The $^1$H-NMR spectrum of $Mg_2(DOBDC)(MeOH)_2$ is shown in FIG. 9. The FT-IR spectrum of $Mg_2(DOBDC)(MeOH)_2$ is shown in FIG. 10. The thermogravimetric analysis (TGA) data of $Mg_2(DOBDC)(MeOH)_2$ are shown in FIG. 11. The nitrogen adsorption isotherm of $Mg_2(DOBDC)(MeOH)_2$ at 77 K is shown in FIG. 12. The BET surface area was 1763 m$^2$/g.

A remarkably improved effect was demonstrated considering that a BET surface area of 1,500 m$^2$/g or greater has never been reported for the same or similar material. The increased adsorption attributable to the increased vacant sites of the metal for adsorption of carbon dioxide and carbon monoxide. The prepared adsorbent can maintain superior adsorption characteristics even with decreased amount.

Example 10

Figure 13:
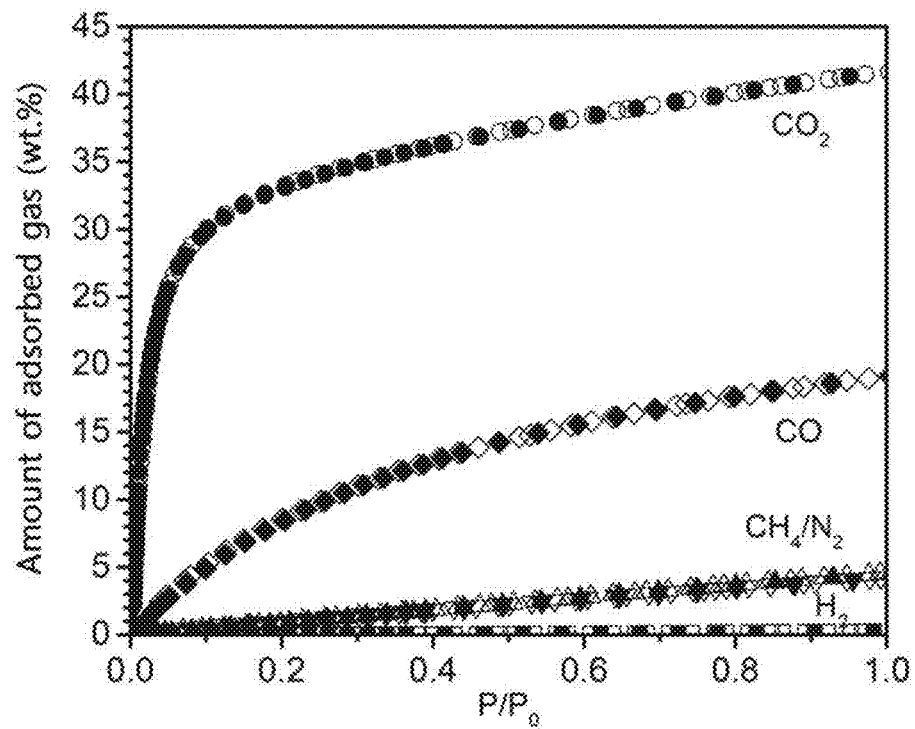
FIG. 13 shows the carbon dioxide, carbon monoxide, nitrogen, hydrogen and methane adsorption isotherms of [$Mg_2$(DOBDC)] at 298 K after pretreatment.
Figure 14:
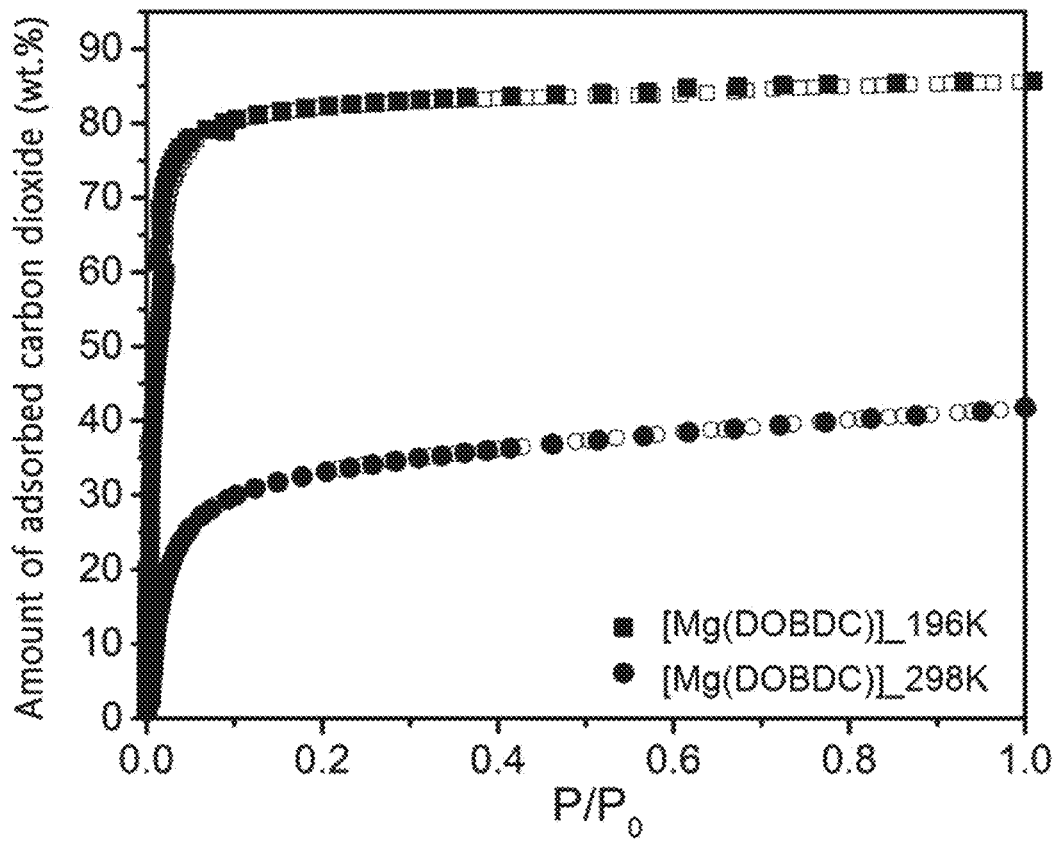
FIG. 14 shows the carbon dioxide adsorption isotherms of [$Mg_2$(DOBDC)] at 196 K and 298 K after pretreatment.

The carbon dioxide, carbon monoxide, nitrogen, methane and hydrogen adsorption isotherms of $Mg_2(DOBDC)$ at room temperature are shown in FIG. 13. High selectivity is observed for carbon dioxide and carbon monoxide. Also, the carbon dioxide adsorption isotherm of $Mg_2(DOBDC)$ measured at 196 K is shown in FIG. 14. When saturated with carbon dioxide, the maximum amount of carbon dioxide adsorbed on $Mg_2(DOBDC)$ was 86 wt % (19.5 mmol/g).

Example 11

Figure 15:
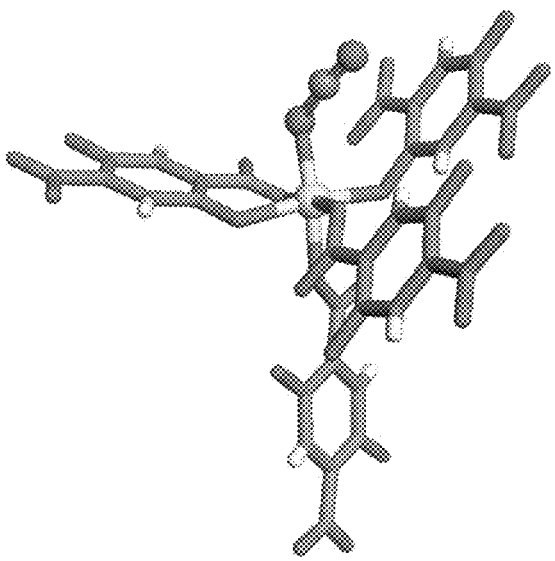
FIG. 15 shows the single crystal X-ray diffraction structure of [$Mg_2$(DOBDC)] on which carbon dioxide is adsorbed.

In order to investigate the adsorption site of carbon dioxide, single crystal X-ray diffraction experiment was conducting using a synchrotron accelerator after pretreatment of $Mg_2(DOBDC)$ and adsorption of carbon dioxide. As a result, it was confirmed that the solvent molecule bound to the metal ion of $Mg_2(DOBDC)$ had been completely removed and carbon dioxide was bound thereto. The single crystal X-ray diffraction structure showing carbon dioxide bound to $Mg_2(DOBDC)$ is shown in FIG. 15.

Comparative Example 1

0.337 g of 2,5-dihydroxy-1,4-benzenedicarboxylic acid, 135 mL of dimethylformamide (DMF), 9.0 mL of ethanol and 9.0 mL of $H_2O$ were used per 1.40 g of $Mg(NO_3)_2 \cdot 6H_2O$. Reaction temperature was 125° C. and reaction time was 48 hours.

Figure 16:
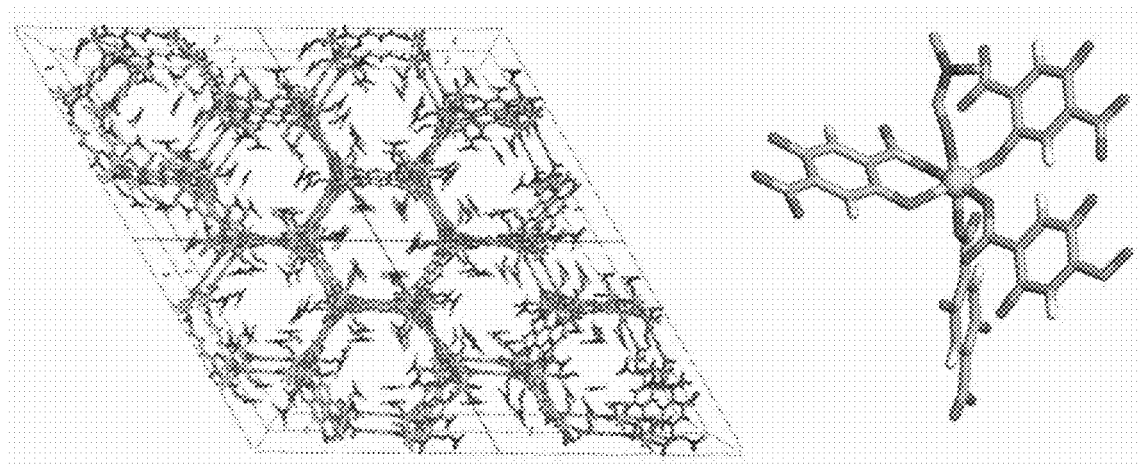
FIG. 16 shows the single crystal X-ray diffraction structure of [$Mg_2$(DOBDC)(DMF)$_2$] synthesized according to the literature.
Figure 17:
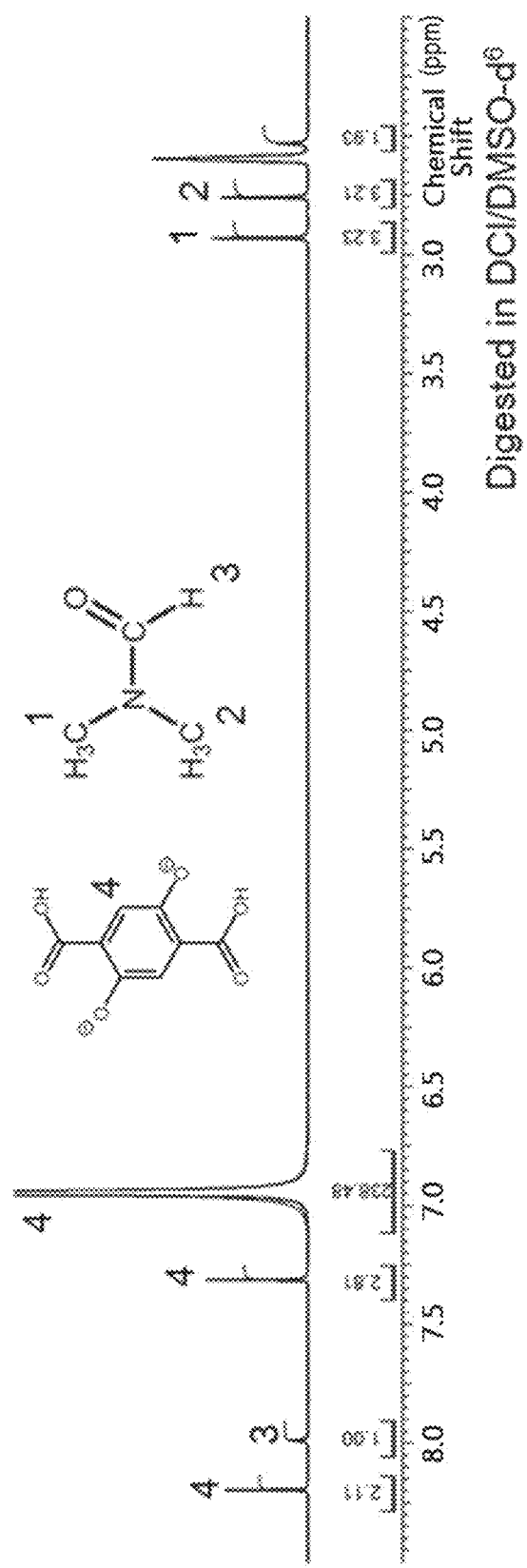
FIG. 17 shows the $^1$H-NMR data of [$Mg_2$(DOBDC)(DMF)$_2$] before pretreatment.

The single crystal X-ray diffraction structure of $Mg_2(DOBDC)(DMF)_2$ prepared according to the existing method is shown in FIG. 16. The single crystal parameters were: trigonal, R-3, a=25.865(4) Å, b=25.865(4) Å, c=6.911(3) Å, α=90°, β=90°, γ=120°, V=4004(1) Å$^3$, Z=9, T=100(2) K, $d_{calc}$=1.474 g/cm$^3$, $R_1$=0.0899 (I>2σ(I)), wR$_2$=0.2826 (all data), GOF=1.298. The $^1$H-NMR spectrum of $Mg_2(DOBDC)(DMF)_2$ is shown in FIG. 17.

Comparative Example 2

Figure 18:
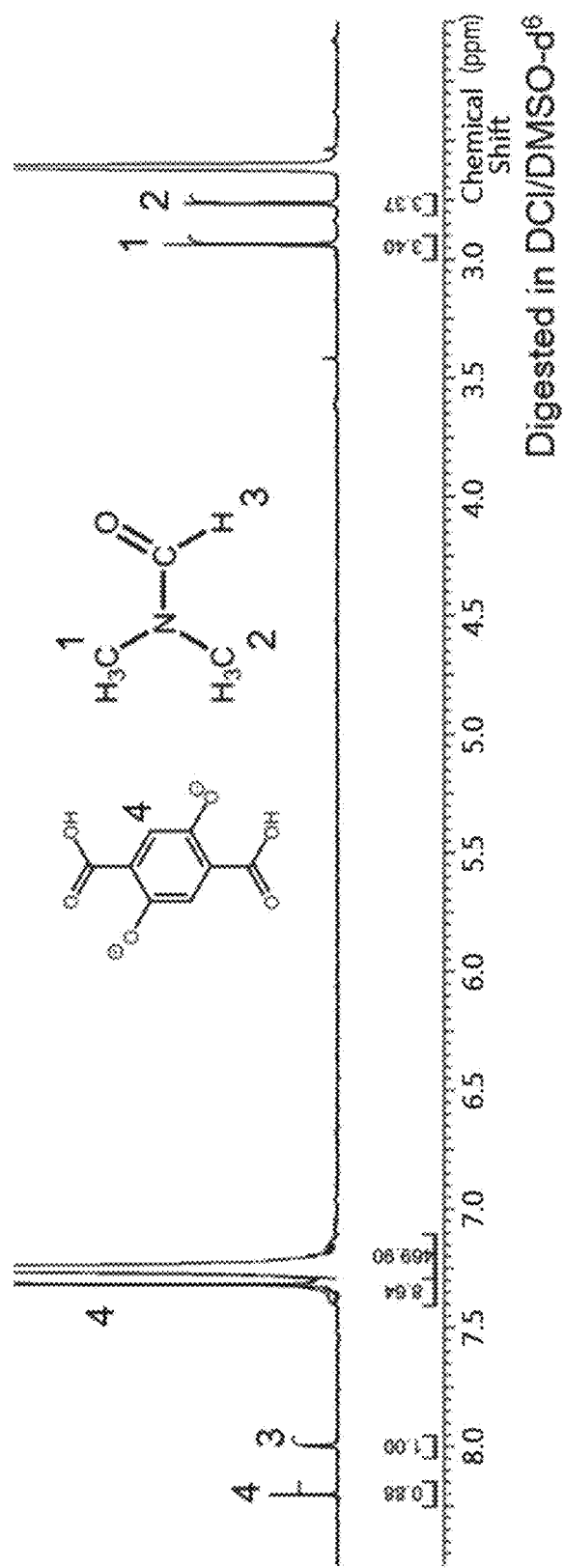
FIG. 18 shows the $^1$H-NMR data of [$Mg_2$(DOBDC)(DMF)$_2$] after pretreatment.
Figure 19:
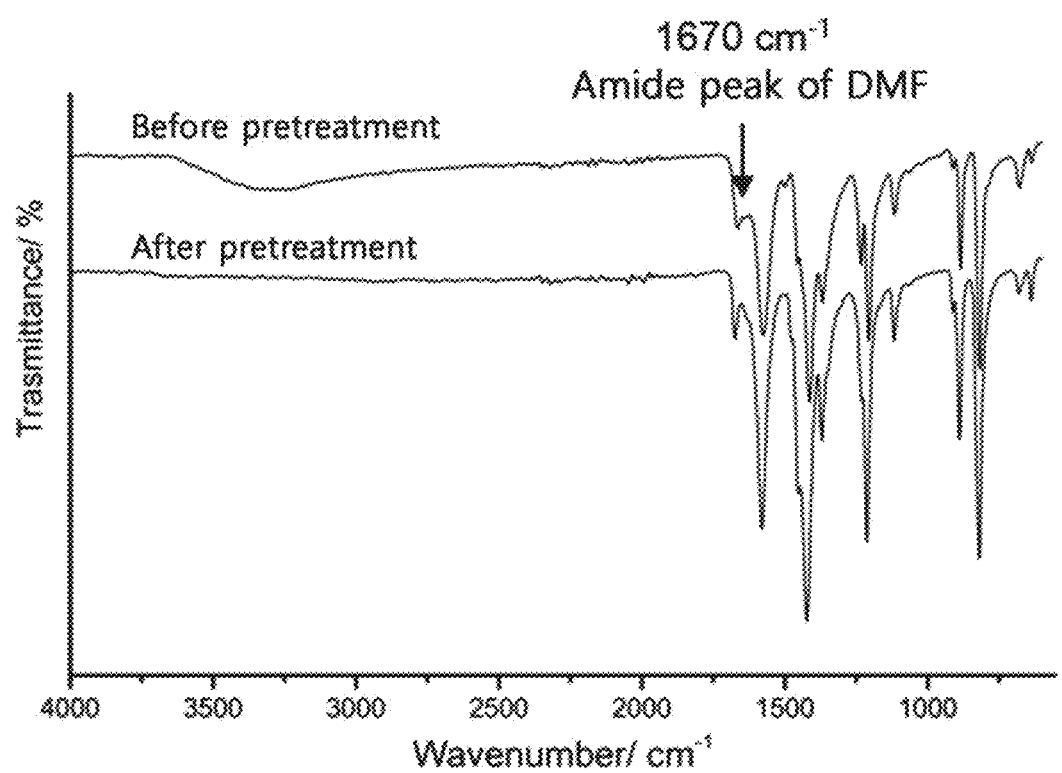
FIG. 19 shows the FT-IR spectra of [$Mg_2$(DOBDC)(DMF)$_2$] before and after pretreatment.
Figure 20:
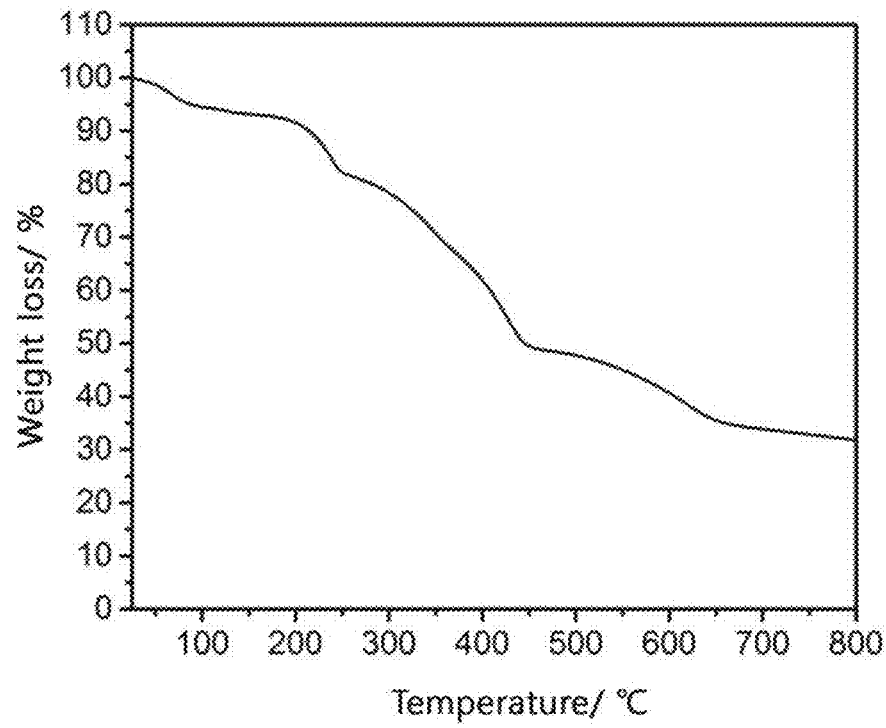
FIG. 20 shows the thermogravimetric analysis (TGA) data of [$Mg_2$(DOBDC)(DMF)$_2$] after pretreatment.
Figure 21:
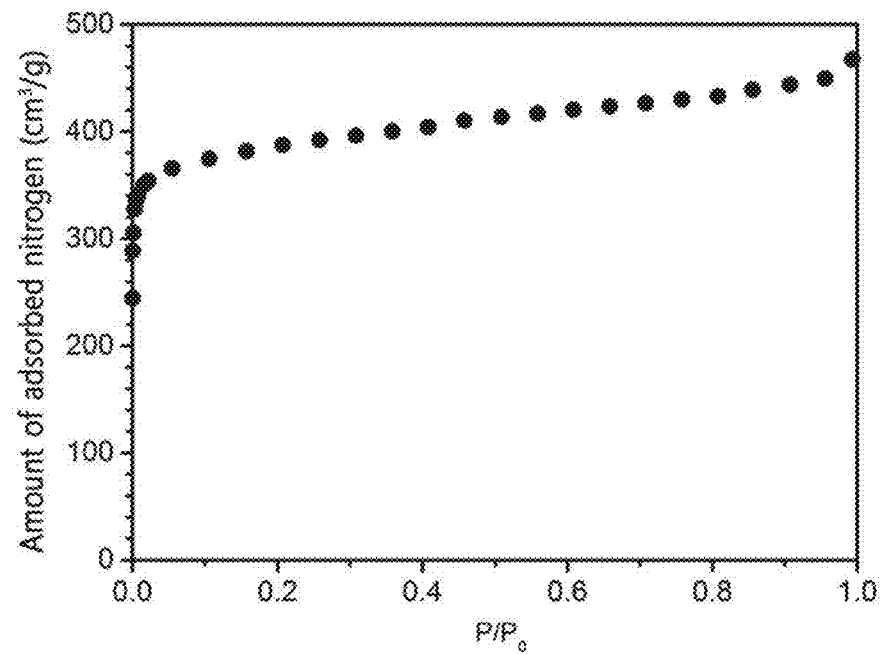
FIG. 21 shows the nitrogen adsorption isotherm of [$Mg_2$(DOBDC)(DMF)$_2$] at 77 K after pretreatment.

In order to completely remove the solvent molecule remaining in the pores of $Mg_2(DOBDC)(DMF)_2$, $Mg_2(DOBDC)(DMF)_2$ was immersed in methanol for 4 days and pretreated by heating at 250° C. for 7 days under a vacuum atmosphere. The $^1$H-NMR spectrum is shown in FIG. 18. The FT-IR spectrum is shown in FIG. 19. The thermogravimetric analysis (TGA) data are shown in FIG. 20. The nitrogen adsorption isotherm at 77 K is shown in FIG. 21. The BET surface area was 1495 m²/g.

Figure 22A:
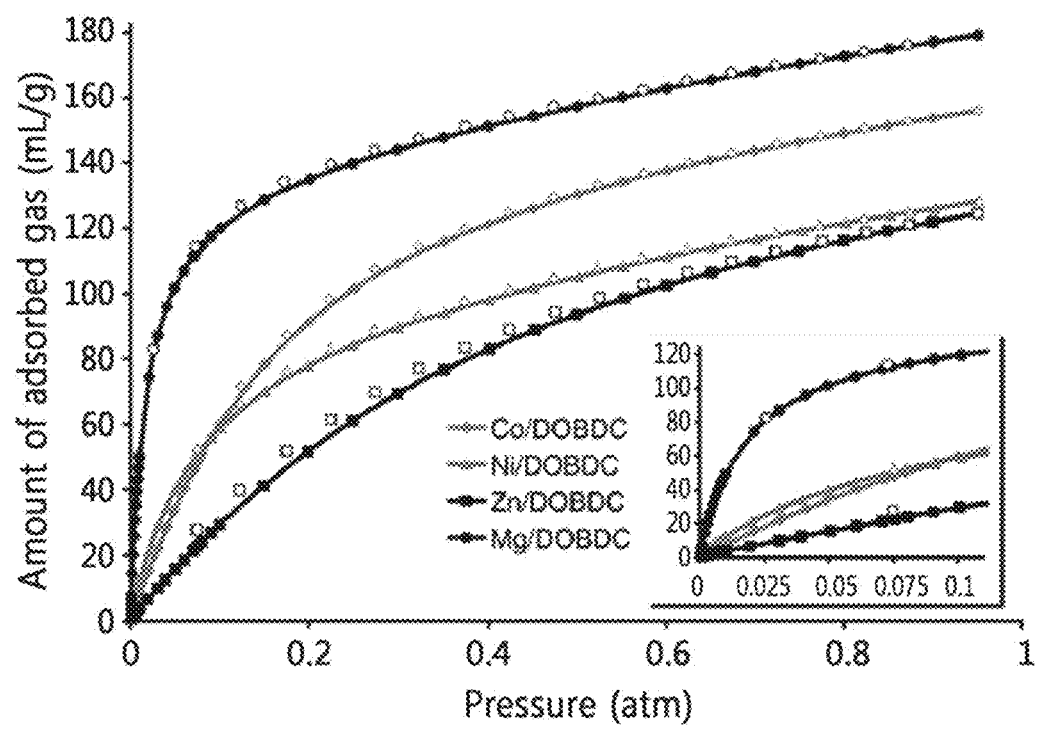
FIG. 22a shows the carbon dioxide adsorption isotherms reported in the literature.
Figures 22B, 22C:
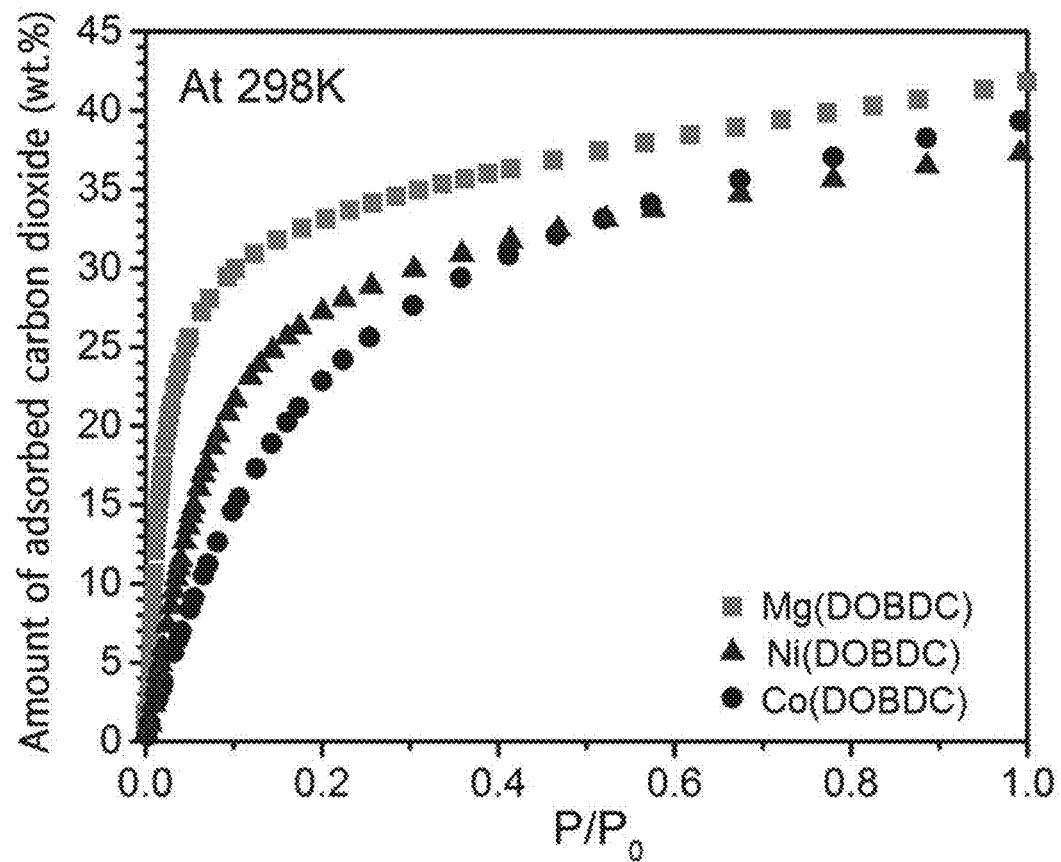
FIG. 22b shows the carbon dioxide adsorption isotherms of materials prepared according to the present disclosure.
FIG. 22c compares the amount of adsorbed carbon dioxide of the metal-organic frameworks according to the literature and the present disclosure.
Figure 22D:
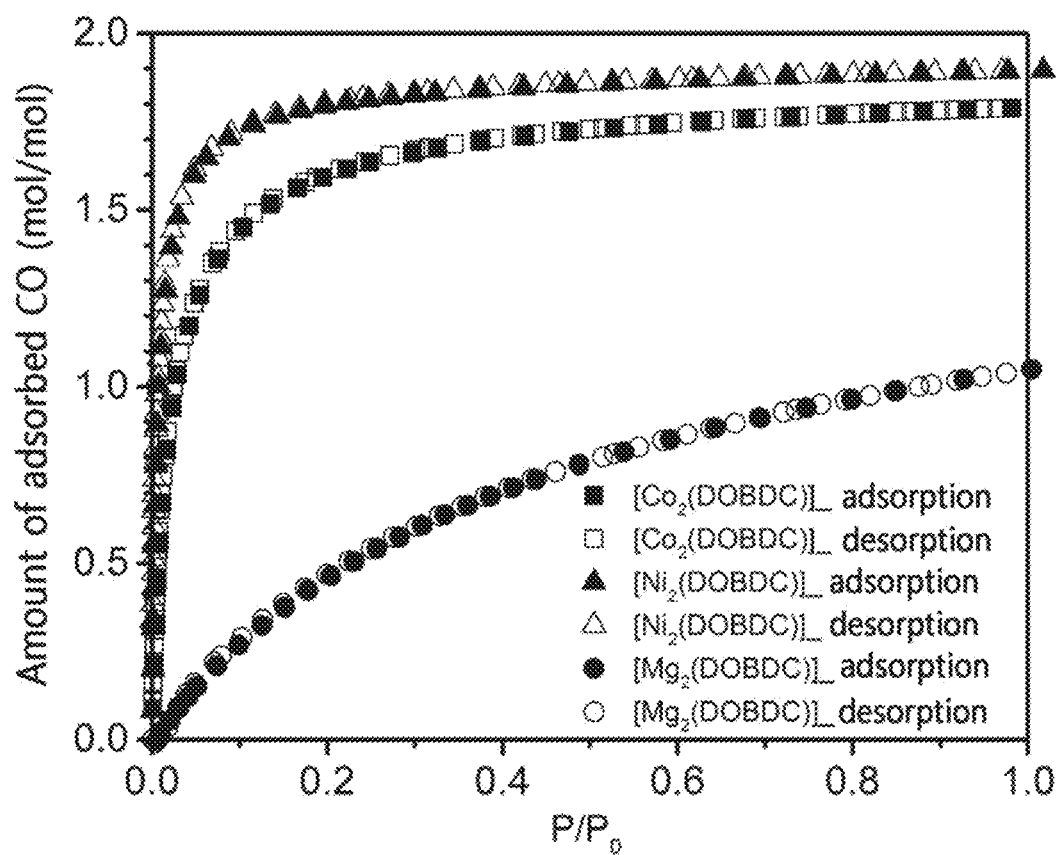
FIG. 22d shows the carbon monoxide isotherms of materials prepared according to the present disclosure.

The metal-organic framework of Comparative Example 1 prepared according to the literature (S. R. Caskey, A. G. Wong-Foy and A. J. Matzger, *J. Am, Chem, Soc.*, 2008, 130, 10870) has the DMF solvent bound to the metal inside the pores, whereas the metal-organic frameworks of Examples 1-8 have the organic solvent having a hydrophilic OH functional group bound to the metal. $M_2(DOBDC)(MeOH)_2$ (M=Mg, Co, Ni, Fe, Mn, Zn, Cu) can be prepared according to Example 8 from $M_2(DOBDC)(EG)_2$ synthesized in Examples 1-7 and $M_2(DOBDC)$ can be prepared therefrom by conducting pretreatment according to Example 9. The prepared metal-organic framework exhibits larger specific surface area and better gas adsorption characteristics than the metal-organic framework prepared in Comparative Example 2. The amount of adsorbed carbon dioxide reported in the literature and the amount of adsorbed carbon dioxide of $M_2(DOBDC)$ (M=Mg, Co, Ni) pretreated according to Example 9 are shown in FIG. 22*a*, FIG. 22*b* and FIG. 22*c*. The amount of absorbed carbon monoxide for $M_2(DOBDC)$ (M=Mg, Co, Ni) pretreated according to Example 9 is shown in FIG. 22*d*.

What is claimed is:

1. A method for preparing a metal-organic framework comprising Chemical Formula 4a, the method comprising:
    (A) preparing a solution comprising (i) one or more metal precursor selected from $M^1A^1_{y1}.x^1H_2O$, $M^2A^2_{y2}.x^2H_2O$, $M^3A^3_{y3}.x^3H_2O$, $M^4A^4_{y4}.x^4H_2O$ and $M^5A^5_{y5}.x^5H_2O$; (ii) 2,5-dihydroxy-1,4-benzenedicarboxylic acid or a derivative thereof; (iii) $S^1_{OH}$; (iv) an amine-based first additive; and (v) one or more second additive selected from diethylformamide, dimethylacetamide, benzylamine, diisopropylformamide and dimethylformamide and obtaining a metal-organic framework comprising Chemical Formula 4a by conducting a reaction:
    Chemical Formula 4a

    $$M^1_{n1}M^2_{n2}M^3_{n3}M^4_{n4}M^5_{n5}(DOBDC)(S^1_{OH})_2 \quad (4a)$$

wherein DOBDC is negatively charged, tetravalent 2,5-dioxido-1,4-benzenedicarboxylate,
    wherein n1, n2, n3, n4 and n5 are real numbers which are equal to or greater than 0 and satisfy n1+n2+n3+n4+n5=2;
    each of $M^1$, $M^2$, $M^3$, $M^4$ and $M^5$, which are different from each other, is independently a divalent metal;
    each of $A^1$, $A^2$, $A^3$, $A^4$ and $A^5$, which are identical to or different from each other, is independently a monovalent anion selected from $NO_3^-$, $Cl^-$, $ClO_4^-$, $OH^-$ and $CH_3CO_2^-$ or a divalent anion selected from $ClO_4^{2-}$, $SO_4^{2-}$ and $CO_3^{2-}$;
    each of $x^1$, $x^2$, $x^3$, $x^4$ and $x^5$, which are identical to or different from each other, is independently an integer from 1 to 50;
    if $A^1$ is a monovalent anion or a divalent anion then y1 is 2 or 1, respectively, if $A^2$ is a monovalent anion or a divalent anion then y2 is 2 or 1, respectively, if $A^3$ is a monovalent anion or a divalent anion then y3 is 2 or 1, respectively, if $A^4$ is a monovalent anion or a divalent anion then y4 is 2 or 1, respectively, and if $A^5$ is a monovalent anion or a divalent anion then y5 is 2 or 1, respectively;
    the derivative of 2,5-dihydroxy-1,4-benzenedicarboxylic acid is one or more selected from a dehydrogenated ion or salt of 2,5-dihydroxy-1,4-benzenedicarboxylic acid;

$S^1_{OH}$ is an organic solvent comprising a hydroxyl group and is used in an amount of 50-95 vol % based on the total volume of the solution; and the second additive is used in an amount of 5-50% based on the total volume of the solution and 1-100% based on the volume of $S^1_{OH}$.

2. A method for preparing a metal-organic framework comprising Chemical Formula 4b, the method comprising:
    (A) preparing a solution comprising (i) one or more metal precursor selected from $M^1A^1_{y1}.x^1H_2O$, $M^2A^2_{y2}.x^2H_2O$, $M^3A^3_{y3}.x^3H_2O$, $M^4A^4_{y4}.x^4H_2O$ and $M^5A^5_{y5}.x^5H_2O$; (ii) 2,5-dihydroxy-1,4-benzenedicarboxylic acid or a derivative thereof; (iii) $S^1_{OH}$; (iv) an amine-based first additive; and (v) one or more second additive selected from diethylformamide, dimethylacetamide, benzylamine, diisopropylformamide and dimethylformamide and obtaining a metal-organic framework comprising Chemical Formula 4a by conducting a reaction:
    Chemical Formula 4a

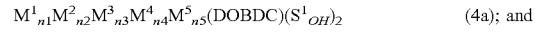
    $$M^1_{n1}M^2_{n2}M^3_{n3}M^4_{n4}M^5_{n5}(DOBDC)(S^1_{OH})_2 \quad (4a); \text{ and}$$

(B) obtaining a metal-organic framework comprising Chemical Formula 4b by contacting the metal-organic framework comprising Chemical Formula 4a with $S^2_{OH}$:
    Chemical Formula 4b

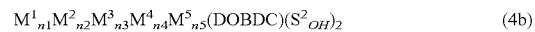
    $$M^1_{n1}M^2_{n2}M^3_{n3}M^4_{n4}M^5_{n5}(DOBDC)(S^2_{OH})_2 \quad (4b)$$

wherein n1, n2, n3, n4 and n5 are real numbers which are equal to or greater than 0 and satisfy n1+n2+n3+n4+n5=2;
    each of $M^1$, $M^2$, $M^3$, $M^4$ and $M^5$, which are different from each other, is independently a divalent metal;
    each of $A^1$, $A^2$, $A^3$, $A^4$ and $A^5$, which are identical to or different from each other, is independently a monovalent anion selected from $NO_3^-$, $Cl^-$, $ClO_4^-$, $OH^-$ and $CH_3CO_2^-$ or a divalent anion selected from $ClO_4^{2-}$, $SO_4^{2-}$ and $CO_3^{2-}$;
    each of $x^1$, $x^2$, $x^3$, $x^4$ and $x^5$, which are identical to or different from each other, is independently an integer from 1 to 50;
    if $A^1$ is a monovalent anion or a divalent anion then y1 is 2 or 1, respectively, if $A^2$ is a monovalent anion or a divalent anion then y2 is 2 or 1, respectively, if $A^3$ is a monovalent anion or a divalent anion then y3 is 2 or 1, respectively, if $A^4$ is a monovalent anion or a divalent anion then y4 is 2 or 1, respectively, and if $A^5$ is a monovalent anion or a divalent anion then y5 is 2 or 1, respectively;
    the derivative of 2,5-dihydroxy-1,4-benzenedicarboxylic acid is one or more selected from a dehydrogenated ion or salt of 2,5-dihydroxy-1,4-benzenedicarboxylic acid;
    $S^1_{OH}$ is a first organic solvent comprising a hydroxyl group and $S^2_{OH}$ is a second organic solvent comprising a hydroxyl group;
    $S^1_{OH}$ is used in an amount of 50-95 vol % based on the total volume of the solution; and
    the second additive is used in an amount of 5-50% based on the total volume of the solution and 1-100% based on the volume of $S^1_{OH}$.

3. A method for preparing a metal-organic framework comprising Chemical Formula 1e, the method comprising:
    (A) preparing a solution comprising (i) one or more metal precursor selected from $M^1A^1_{y1}.x^1H_2O$, $M^2A^2_{y2}.x^2H_2O$, $M^3A^3_{y3}.x^3H_2O$, $M^4A^4_{y4}.x^4H_2O$ and $M^5A^5_{y5}.x^5H_2O$; (ii) 2,5-dihydroxy-1,4-benzenedicarboxylic acid or a derivative thereof; (iii) $S^1_{OH}$; (iv) an amine-based first additive; and (v) one or more second additive selected from diethylformamide, dimethylacetamide, benzylamine, diisopropylformamide and dimethylformamide and obtaining a metal-organic framework comprising Chemical Formula 4a by conducting a reaction:

Chemical Formula 4a

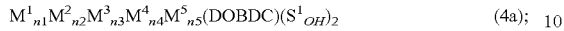

(4a);

(B) obtaining a metal-organic framework comprising Chemical Formula 4b by contacting the metal-organic framework comprising Chemical Formula 4a with $S^2_{OH}$:

Chemical Formula 4b

(4b); and (C) obtaining a metal-organic framework comprising Chemical Formula 1e by drying the metal-organic framework comprising Chemical Formula 4b:

Chemical Formula 1e

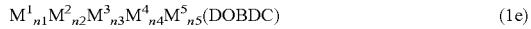

(1e)

wherein n1, n2, n3, n4 and n5 are real numbers which are equal to or greater than 0 and satisfy n1+n2+n3+n4+n5=2;

each of $M^1$, $M^2$, $M^3$, $M^4$ and $M^5$, which are different from each other, is independently a divalent metal;

each of $A^1$, $A^2$, $A^3$, $A^4$ and $A^5$, which are identical to or different from each other, is independently a monovalent anion selected from $NO_3^-$, $Cl^-$, $ClO_4^-$, $OH^-$ and $CH_3CO_2^-$ or a divalent anion selected from $ClO_4^{2-}$, $SO_4^{2-}$ and $CO_3^{2-}$;

each of $x^1$, $x^2$, $x^3$, $x^4$ and $x^5$, which are identical to or different from each other, is independently an integer from 1 to 50;

if $A^1$ is a monovalent anion or a divalent anion then y1 is 2 or 1, respectively, if $A^2$ is a monovalent anion or a divalent anion then y2 is 2 or 1, respectively, if $A^3$ is a monovalent anion or a divalent anion then y3 is 2 or 1, respectively, if $A^4$ is a monovalent anion or a divalent anion then y4 is 2 or 1, respectively, and if $A^5$ is a monovalent anion or a divalent anion then y5 is 2 or 1, respectively;

the derivative of 2,5-dihydroxy-1,4-benzenedicarboxylic acid is one or more selected from a dehydrogenated ion or salt of 2,5-dihydroxy-1,4-benzenedicarboxylic acid;

$S^1_{OH}$ is a first organic solvent comprising a hydroxyl group and $S^2_{OH}$ is a second organic solvent comprising a hydroxyl group;

$S^1_{OH}$ is used in an amount of 50-95 vol % based on the total volume of the solution; and the second additive is used in an amount of 5-50% based on the total volume of the solution and 1-100% based on the volume of $S^1_{OH}$.

* * * * *